United States Patent [19] [11] Patent Number: 4,914,083
Wiegers et al. [45] Date of Patent: Apr. 3, 1990

[54] OXY-SUBSTITUTED-2-PHENYL PYRAN DERIVATIVES AND PROCESS FOR PREPARING SAME AND PERFUMERY USES THEREOF

[75] Inventors: Wilhelmus J. Wiegers, Red Bank; Anton Van Ouwerkerk, Livingston, both of N.J.

[73] Assignee: International Flavors & Fragrances Inc., New York, N.Y.

[21] Appl. No.: 380,081

[22] Filed: Jul. 14, 1989

[51] Int. Cl.$^4$ .................................................. A61K 7/46
[52] U.S. Cl. .................................. 512/12; 252/174.11; 252/8.6; 523/102; 549/427; 512/11
[58] Field of Search .................. 512/11, 12; 549/427; 252/174.11, 816; 523/102

[56] References Cited

U.S. PATENT DOCUMENTS

| 3,681,263 | 8/1972 | Van Der Linde | 512/11 |
| 4,221,679 | 9/1980 | Willis et al. | 512/11 |
| 4,292,244 | 9/1981 | Hoffmann et al. | 549/427 |
| 4,717,506 | 1/1988 | Takada et al. | 512/11 |

FOREIGN PATENT DOCUMENTS

| 7608720 | 2/1977 | Netherlands | 549/427 |
| 620487 | 8/1978 | U.S.S.R. | 512/11 |

OTHER PUBLICATIONS

Bravo et al, Gazz.Chim.Ital., 1984, 114(3–4), 93–102, abstracted at Chem.Abstracts 101:230275b.
Arctander, "Perfume and Flavor Chemicals (Aroma Chemicals)", by Steffen Arctander, Published by The Author 1969, vols. I and II, Monograph Nos.: 2640:Prenol, 1472:Guaicol, 1473:Guaiacol Allylether, 1474:Guaiacol Ethylether, 1477:Guaiacyl Phenylacetate, 2924:Tetrahydro-2-(phenethoxy)-Pyran, 2926:Tetrahydro Pyranyl Crotonate, 3067:Vanillin, 3071:Vanillin Triacetate, 3072: Vanillyl Acetate, 3075:Vanillylidene Diaceate, 3076:Vanillyl Vanillate and 3078:Veratrol.

Primary Examiner—James H. Reamer
Attorney, Agent, or Firm—Arthur L. Liberman

[57] ABSTRACT

Described are oxy-substituted-2-phenyl pyran derivatives defined according to the generic structure:

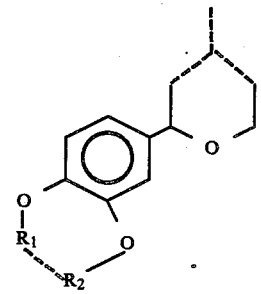

wherein:
(i) the dashed lines in the pyran ring each represents a carbon-carbon single bond; or one of the dashed lines is a carbon-carbon double bond and each of the other of the dashed lines in the pyran ring is a carbon-carbon single bond;
(ii) wherein $R_2$ represents lower alkyl and $R_1$ is hydrogen; or
(iii) $R_1$ and $R_2$ represented by the moiety:

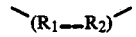

taken together represents methylene and uses thereof in augmenting or enhancing the aroma of perfume compositions, colognes and perfumed articles including but not limited to perfumed polymers, solid or liquid anionic, cationic, nonionic or zwitterionic detergents, fabric softener compositions, fabric softener articles, hair preparations and cosmetic powders.

15 Claims, 12 Drawing Sheets

GLC PROFILE FOR EXAMPLE ONE.

FIG. 2 NMR SPECTRUM FOR EXAMPLE ONE.

GLC PROFILE FOR EXAMPLE TWO.

FIG. 5 NMR SPECTRUM FOR EXAMPLE TWO.

NMR SPECTRUM FOR EXAMPLE THREE.

IR SPECTRUM FOR EXAMPLE THREE.

FIG. 9 GLC PROFILE FOR EXAMPLE FOUR.

NMR SPECTRUM FOR EXAMPLE FOUR.

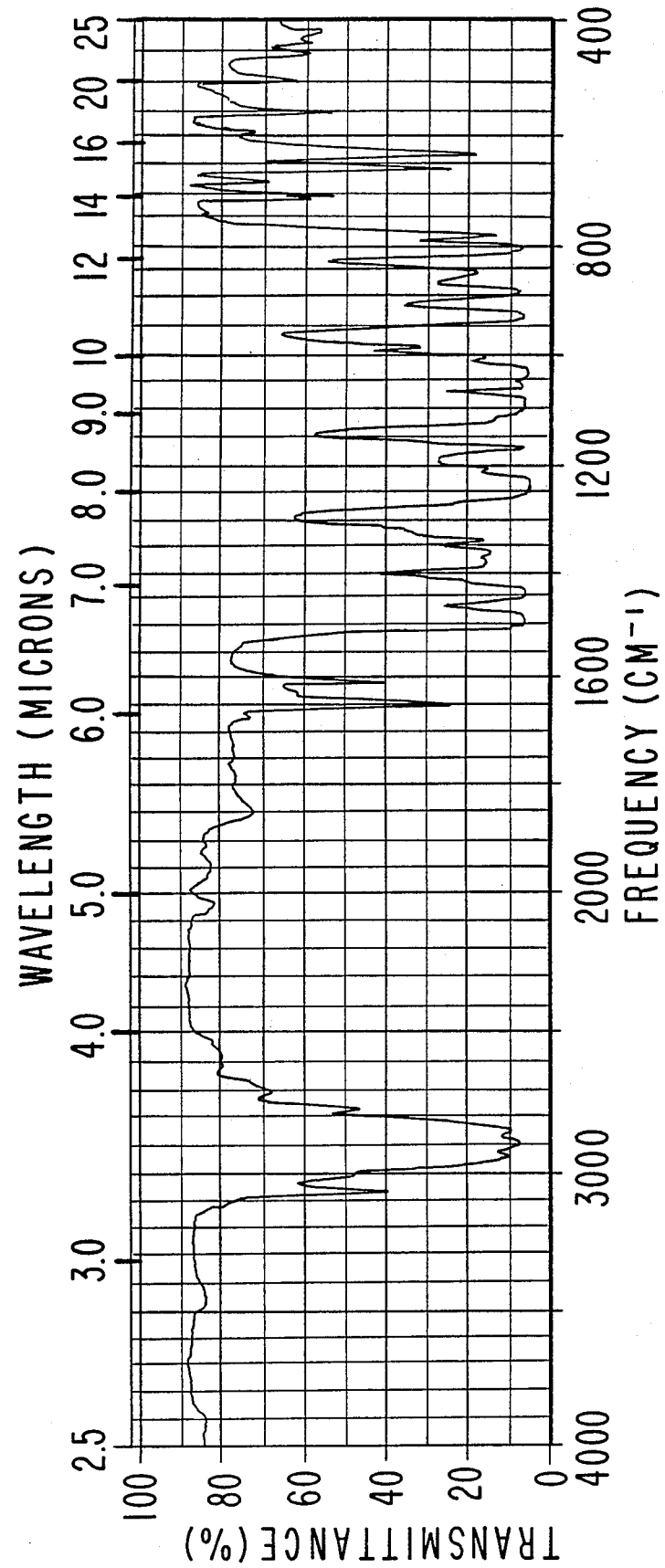

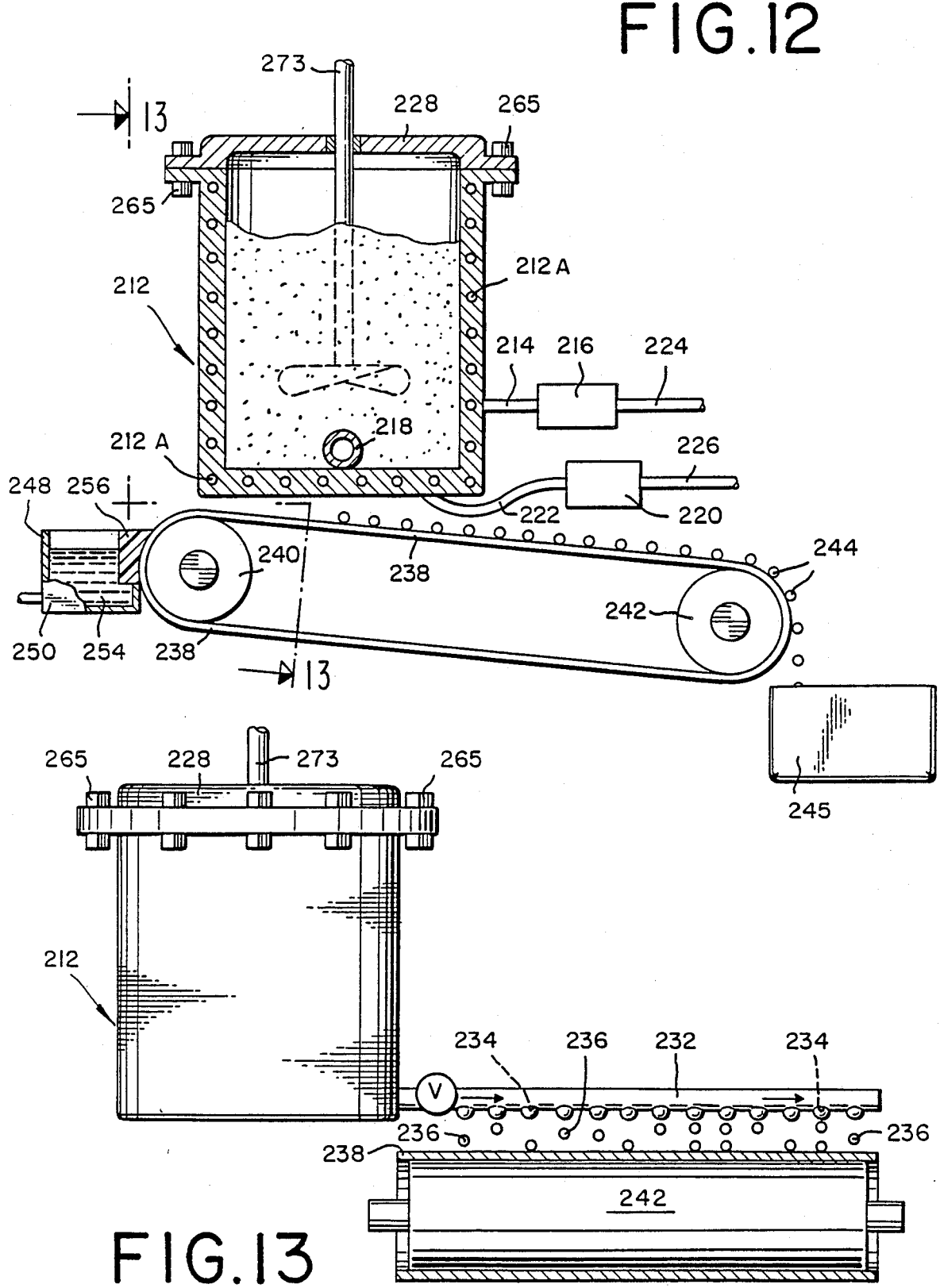

OXY-SUBSTITUTED-2-PHENYL PYRAN DERIVATIVES AND PROCESS FOR PREPARING SAME AND PERFUMERY USES THEREOF

BACKGROUND OF THE INVENTION

This invention relates to oxy-substituted-2-phenyl pyran derivatives defined according to the structure:

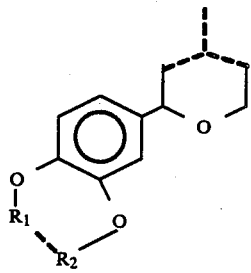

(i) the dashed lines in the pyran ring each represents a carbon-carbon single bond; or one of the dashed lines is a carbon-carbon double bond and the other of the dashed lines is a carbon-carbon single bond;
(ii) $R_2$ represents lower alkyl and $R_1$ represents hydrogen; or
(iii) the moiety $R_1$ and $R_2$ taken together represented by the structure:

is methylene;
and uses thereof in augmenting or enhancing the aroma of perfume compositions, colognes and perfumed articles.

Materials which can provide spicy, floral, rose, vanilla-like, smokey, nutmeg, woody, tonka absolute-like, and balsamic aroma nuances with carnation, floral, rose, guiacwood, balsamic, natural sweet, vanilla, smokey, woody, musky and fruity topnotes are highly desirable in the art of perfumery. Many of the natural substances which provide such fragrance nuances and contribute the desired nuances to perfumery compositions are high in cost, vary in quality from one batch to another and/or are generally subject to the usual variations of natural products.

Oxy-substituted-2-phenyl pyran derivatives are known in the prior art.

Thus, the compound having the structure:

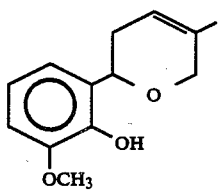

is disclosed by Bravo, et al in Gazz.Chim.Ital., 1984, 114(3-4), 93-102, abstracted at Chemical Abstracts, Volume 101:230275b.

Furthermore, materials having the phenyl and pyran moiety together with ether moieties are known to be useful in the art of perfumery. So, too, is prenol having the structure:

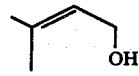

and guiacol having the structure:

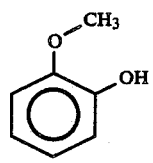

known to be useful in the art of perfumery.

Arctander, "Perfume and Flavor Chemicals (Aroma Chemicals)", at Volumes I and II, (published 1969), at Monograph No. 2924 discloses the use of the compound having the structure:

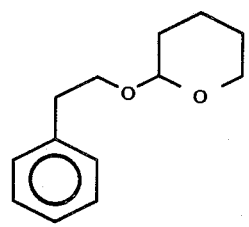

in perfumery. Arctander further discloses at Monograph No. 1472 the use of guaicol having the structure:

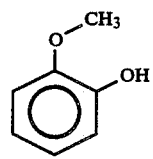

in perfumery. Furthermore, Arctander discloses at Monograph No. 2640 the use of prenol itself having the structure:

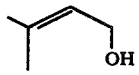

in perfumery. At Monograph No. 3067, Arctander discloses the use of vanillin having the structure:

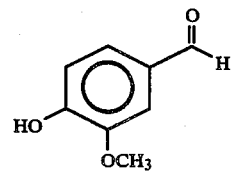

in perfumery.

Nothing in the prior art however discloses the unobvious, unexpected and advantageous utilities of the oxy-substituted-2-phenyl pyran derivatives of our invention in perfumery.

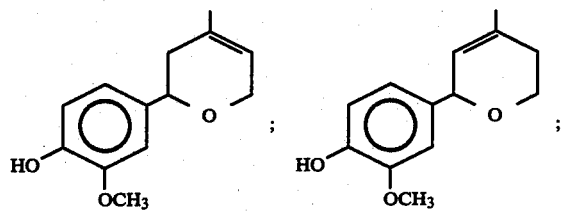

and

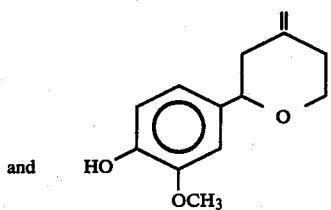

Figure 2:
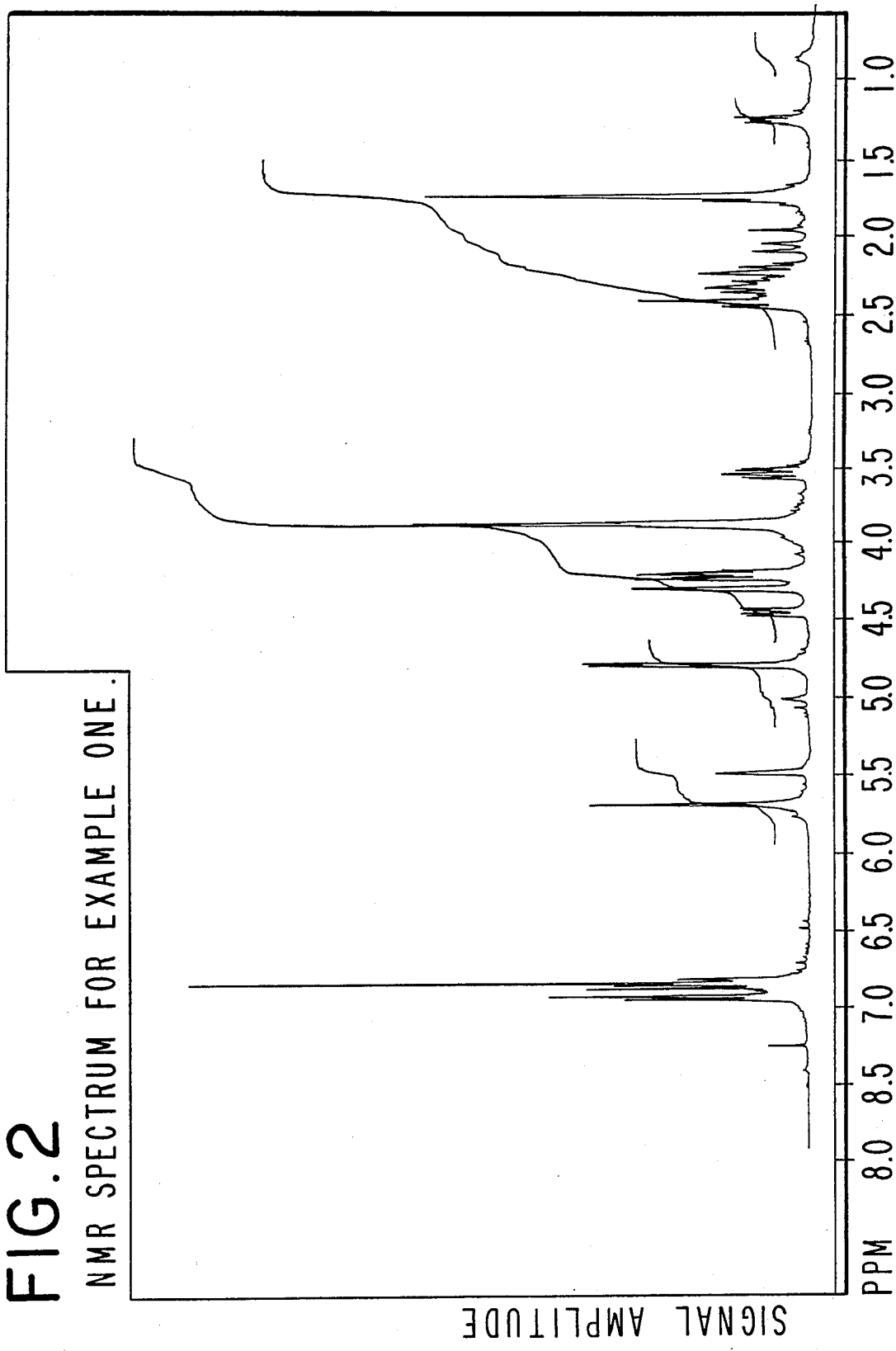

FIG. 2 is the NMR spectrum for the mixture of compounds defined according to the structure:

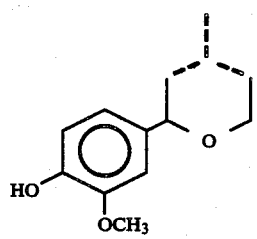

wherein in the mixture in each of the compounds one of the dashed lines is a carbon-carbon double bond and each of the other of the dashed lines represents a carbon-carbon single bond.

Figure 3:
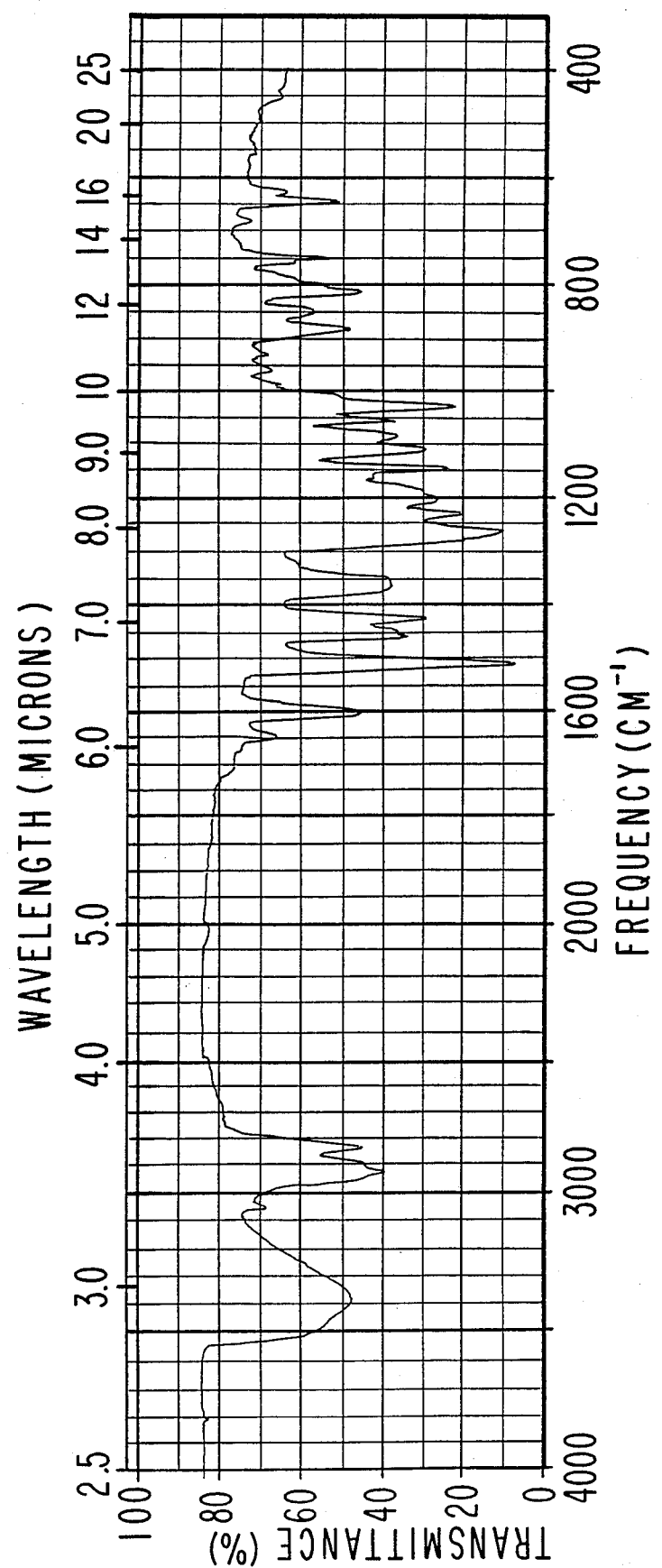

FIG. 3 is the infra-red spectrum for the mixture of compounds produced according to Example I containing compounds defined according to the structure:

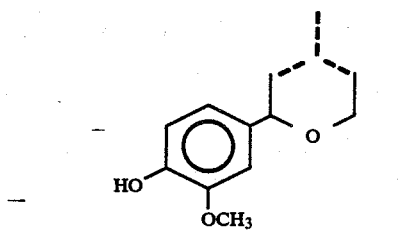

wherein in the mixture each of the compounds one of the dashed lines is a carbon-carbon double bond and each of the other of the dashed lines is a carbon-carbon single bond.

Figure 4:
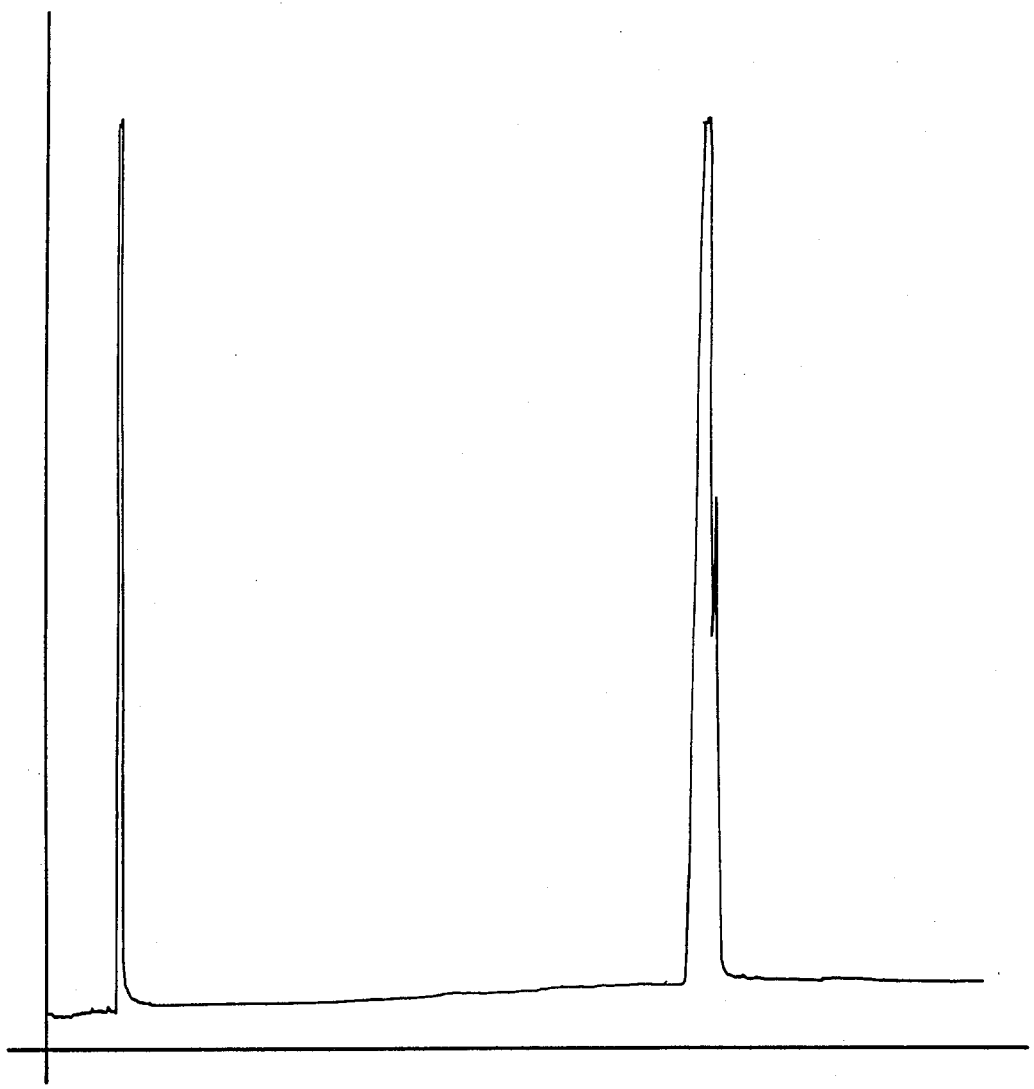

FIG. 4 is the GLC profile for the crude reaction product of Example II containing the compound having the structure:

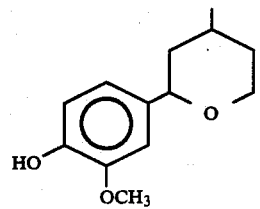

(Conditions: 10% SE-30 column programmed at 80°–220° C.).

Figure 5:
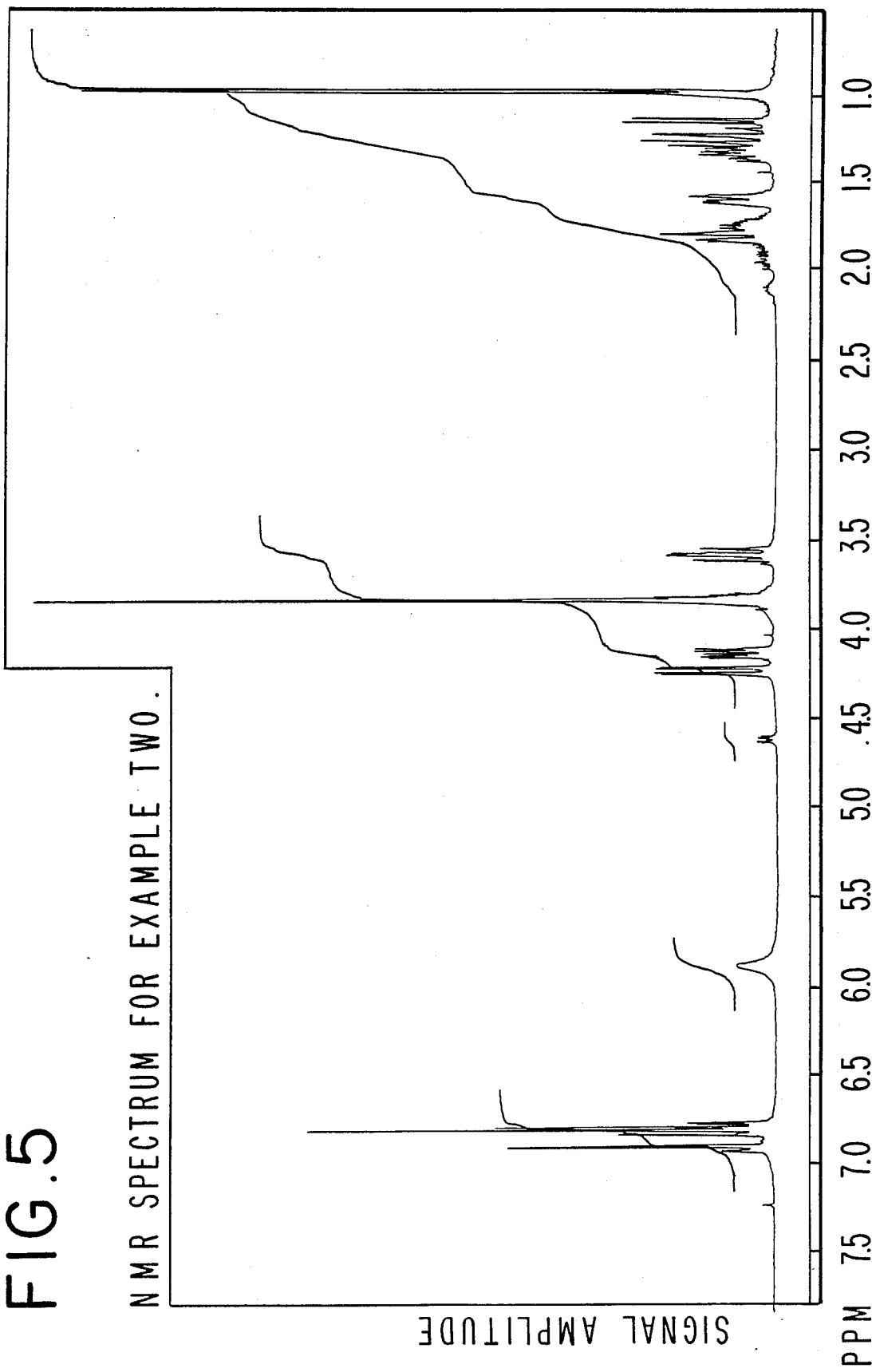

FIG. 5 is the NMR spectrum for the compound having the structure:

produced according to Example II.

Figure 6:
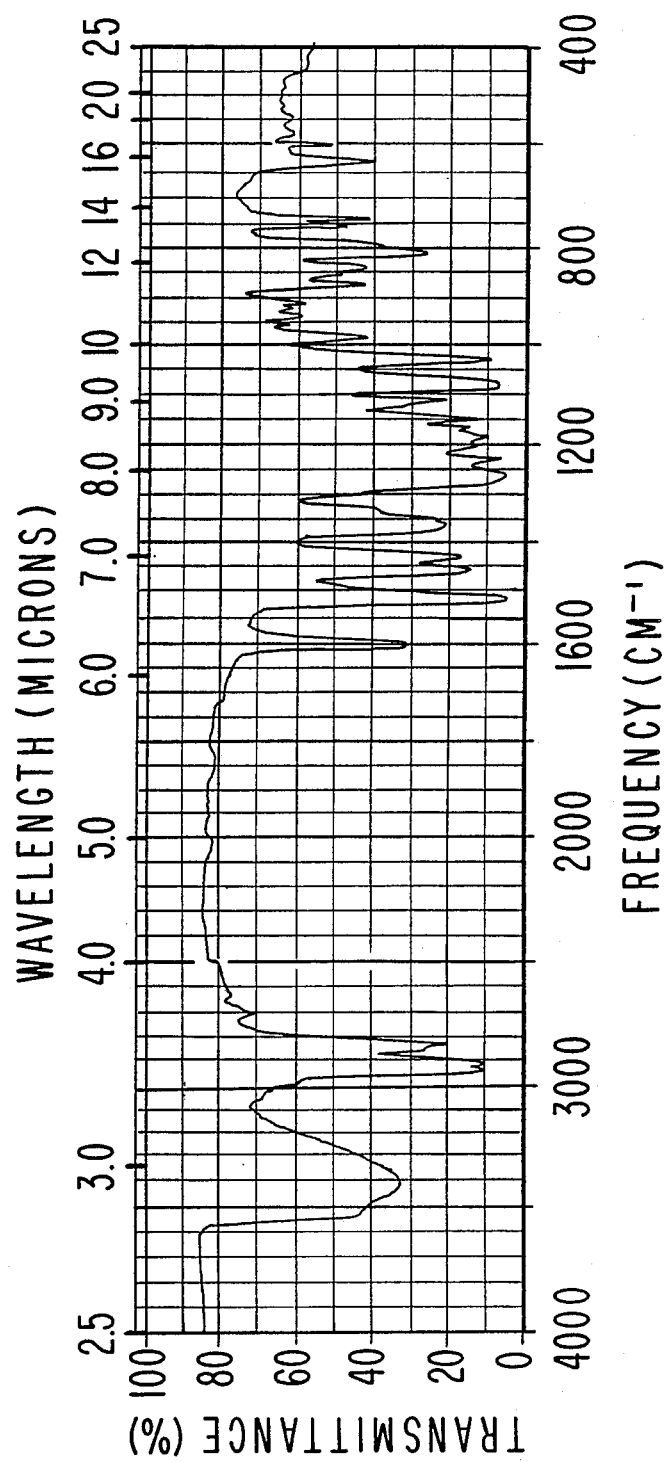

FIG. 6 is the infra-red spectrum for the compound having the structure:

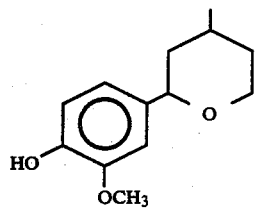

prepared according to Example II.

Figure 7:
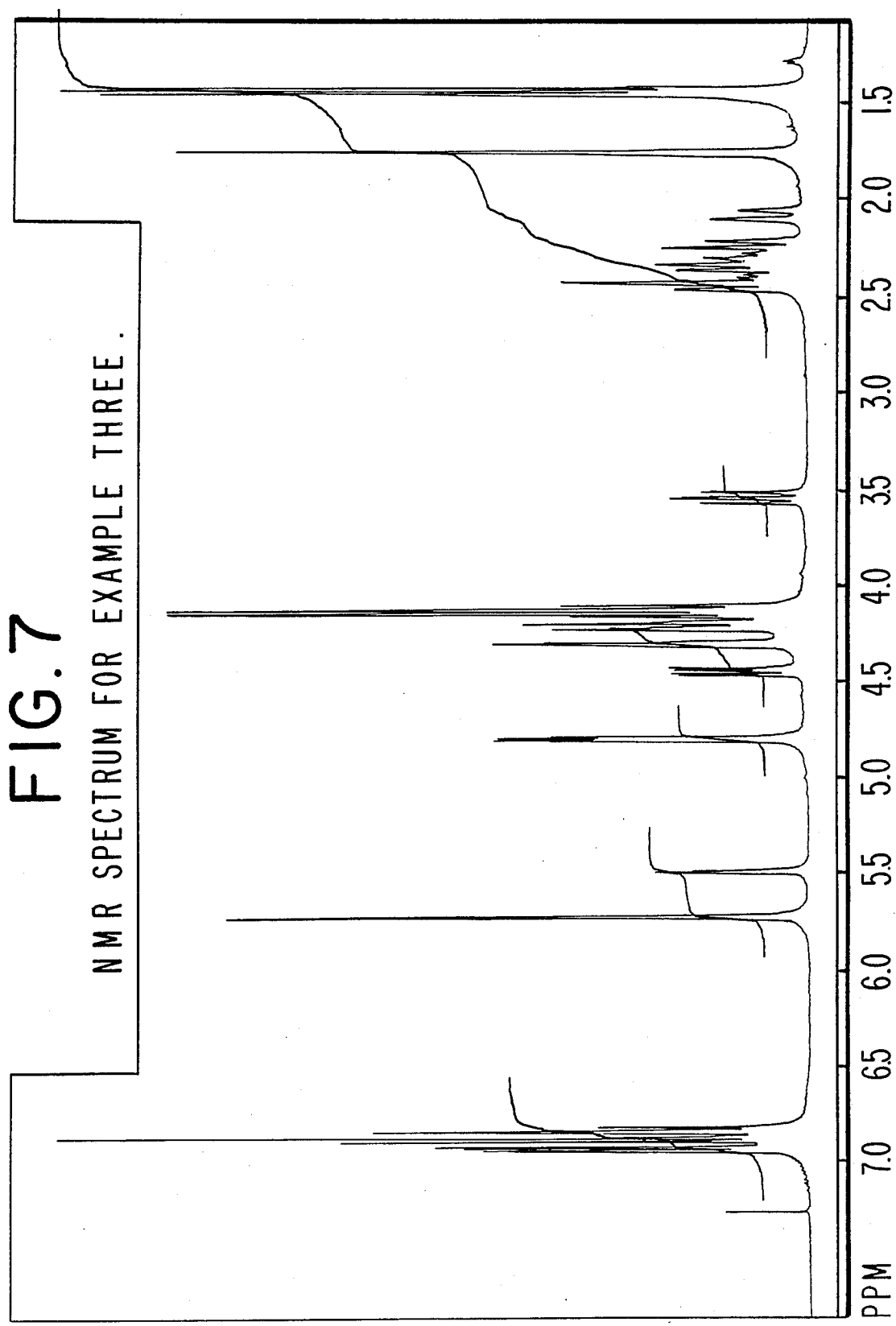

FIG. 7 is the NMR spectrum for the mixture of compounds having the structures:

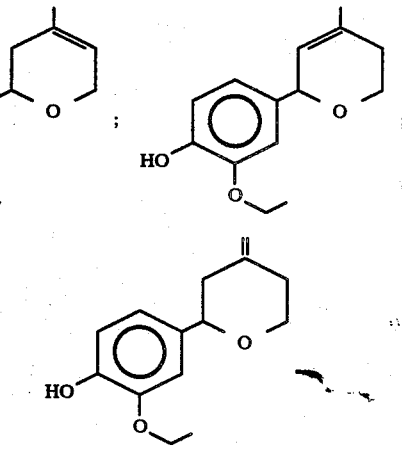

prepared according to Example III.

Figure 8:
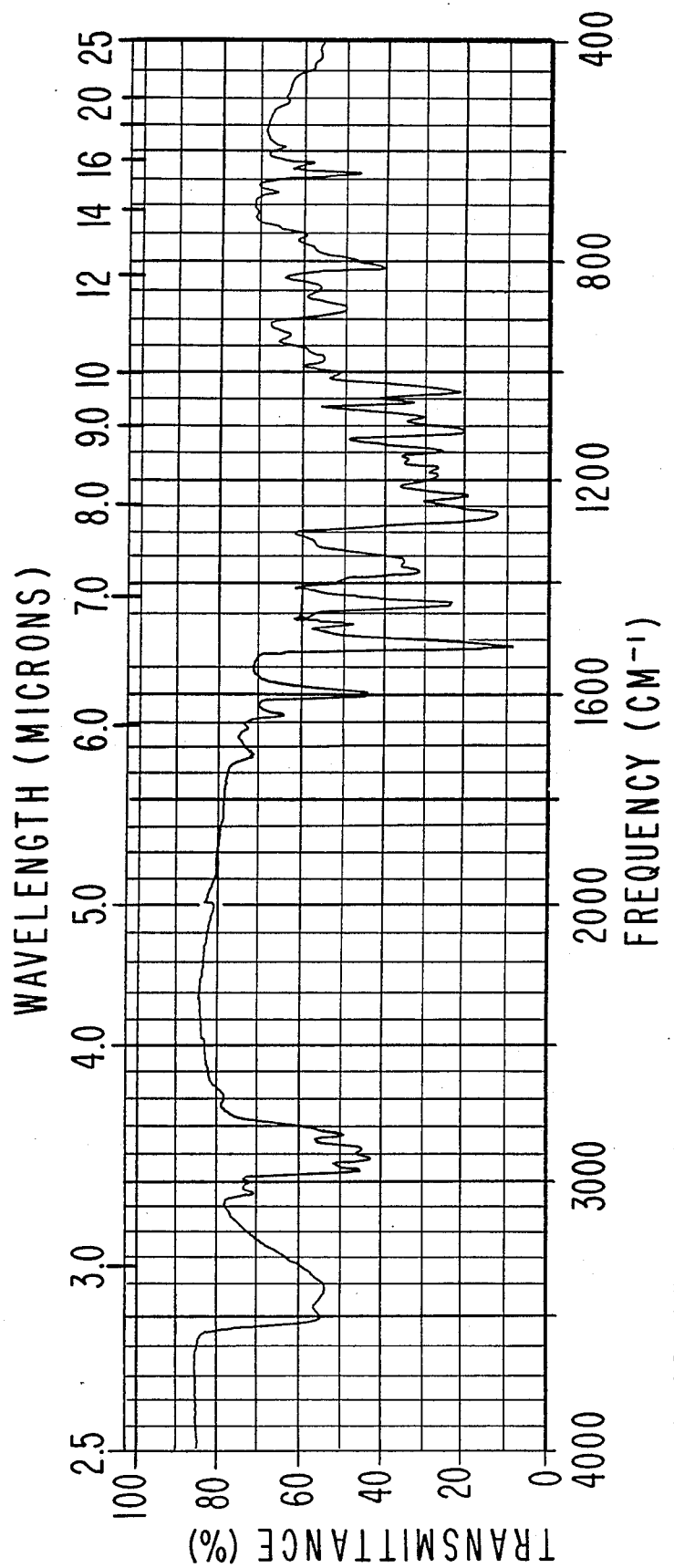

FIG. 8 is the infra-red spectrum for the mixture of compounds defined according to the structure:

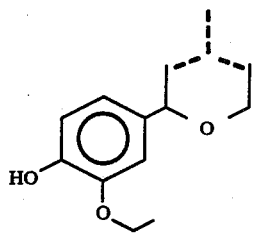

wherein in the mixture in each of the compounds one of the dashed lines is a carbon-carbon double bond and each of the other of the dashed lines is a carbon-carbon single bond.

Figure 9:
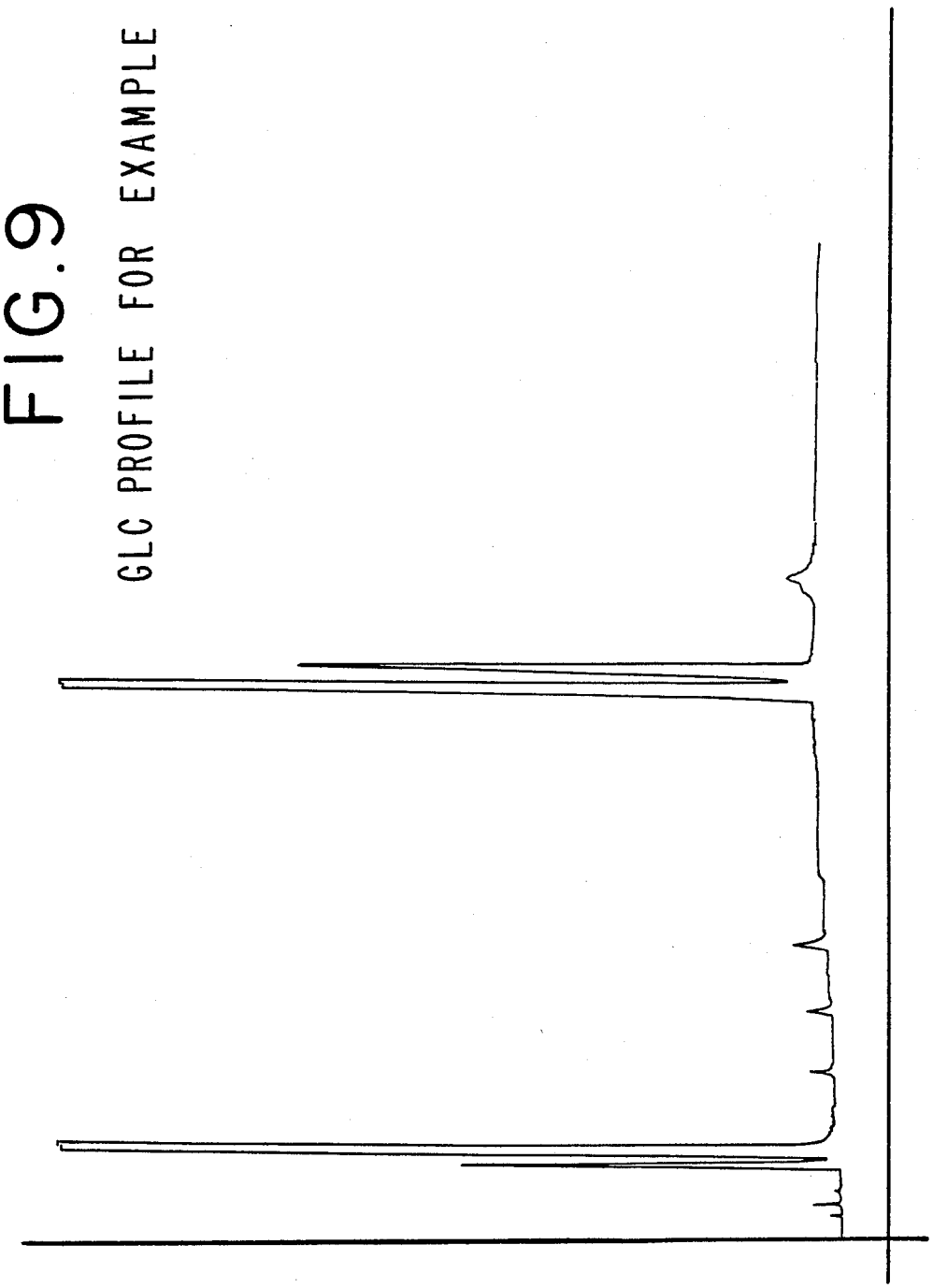

FIG. 9 is the GLC profile for the crude reaction product of Example IV containing the mixture of compounds having the structures:

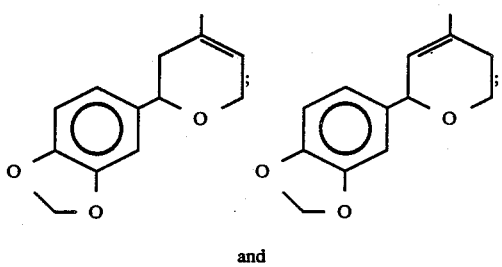

and

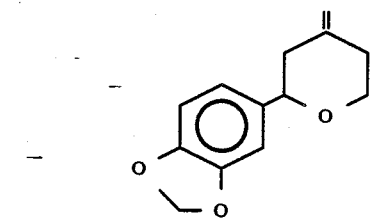

(Conditions: 10% SE-30 column programmed at 80°–220° C. at 8° C. per minute).

Figure 10:
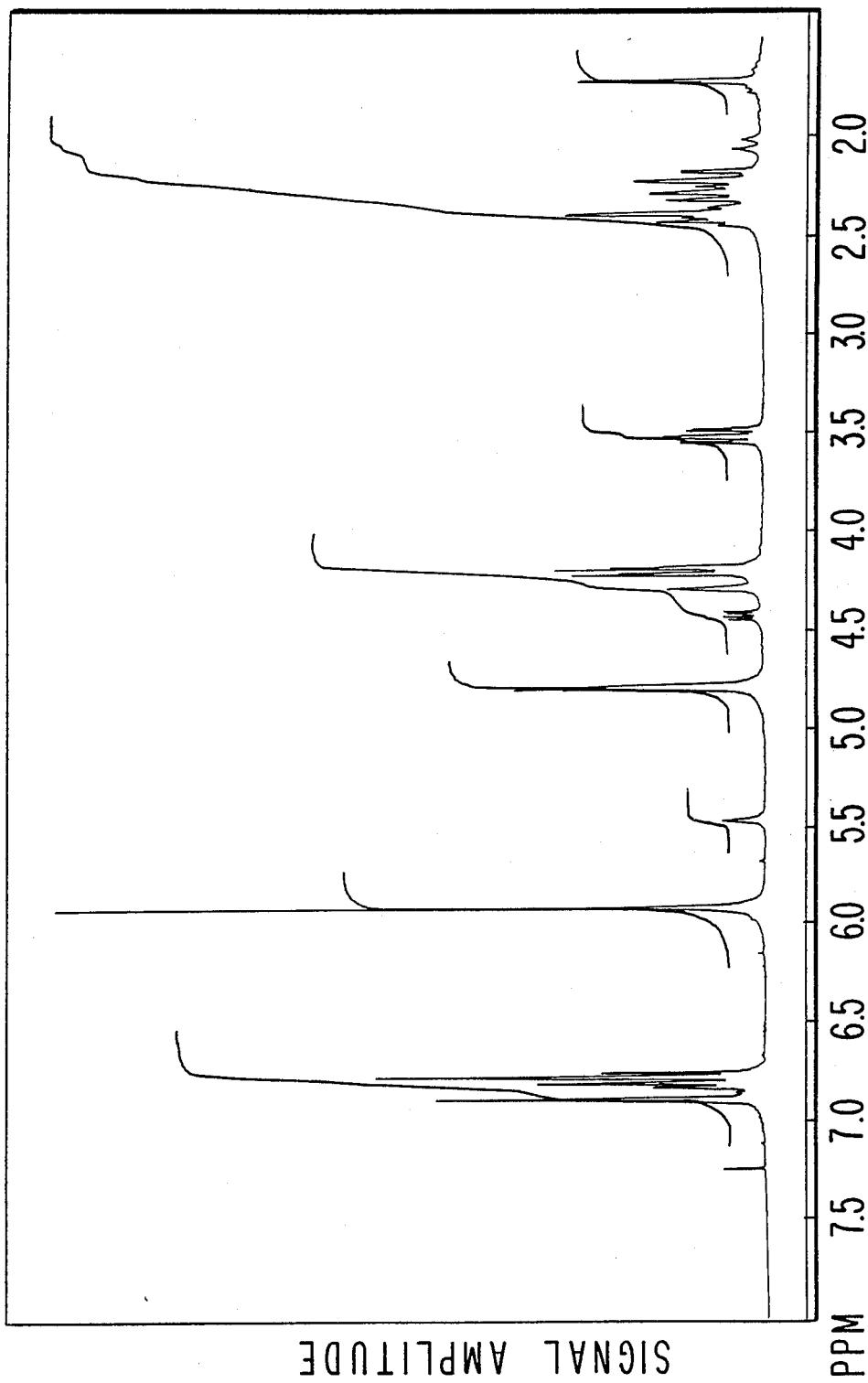

FIG. 10 is the NMR spectrum for the mixture of compounds having the structures:

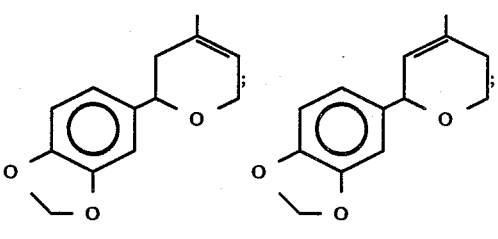

and

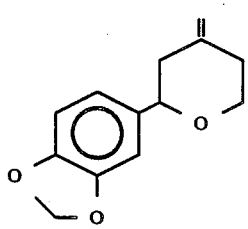

prepared according to Example IV.

FIG. 11 is the infra-red spectrum for the mixture of compounds defined according to the structure:

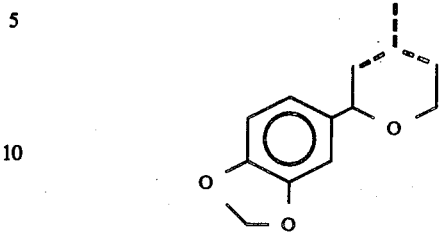

prepared according to Example IV, wherein in the mixture in each of the compounds one of the dashed lines is a carbon-carbon double bond and each of the other of the dashed lines is a carbon-carbon single bond.

FIG. 12 is a partial side elevation and partial sectional view of an apparatus for forming scented polymers using at least one of the oxy-substituted-2-phenyl pyran derivatives of our invention.

FIG. 13 is a section taken on line 13—13 of FIG. 12.

DETAILED DESCRIPTION OF THE DRAWINGS

Figure 1:
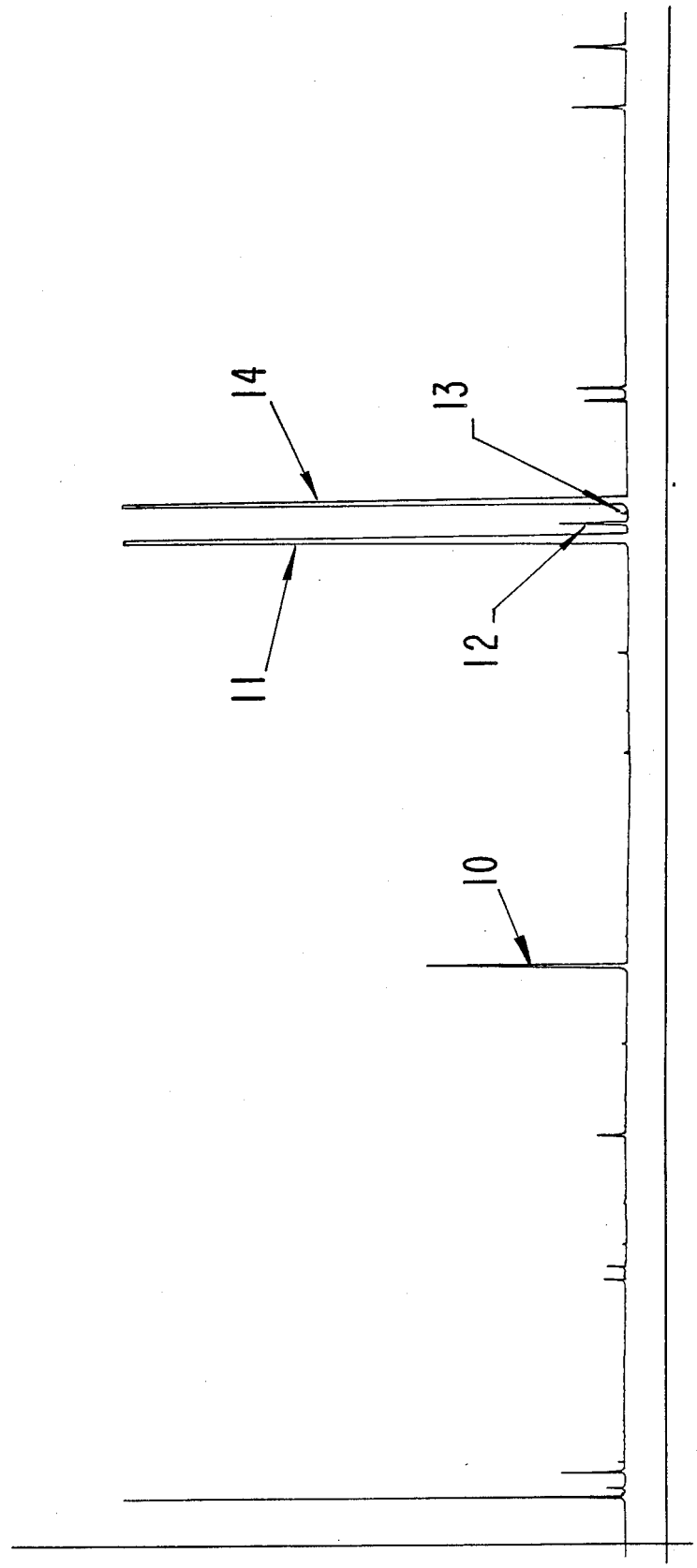
FIG. 1 is the GLC profile for the crude reaction product of Example I containing the compounds defined according to the structures.

FIG. 1 is the GLC profile of the crude reaction product produced according to Example I, containing a mixture of compounds defined according to the structures:

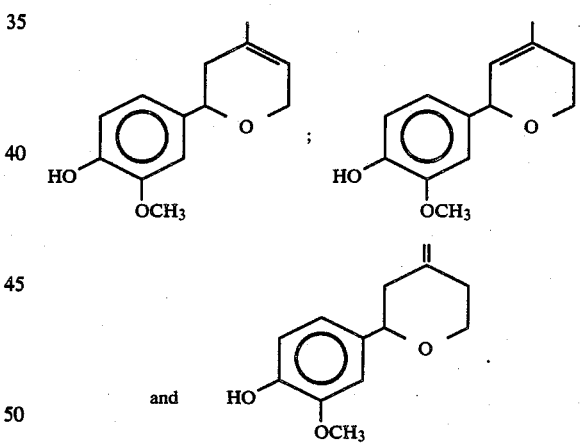

The peak indicated by reference numeral 10 is the peak for the vanillin starting material having the structure:

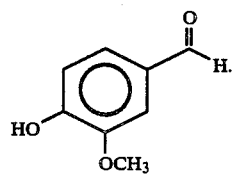

The peaks indicated by reference numerals 11, 12, 13 and 14 are peaks for the isomers of the reaction product having the structures:

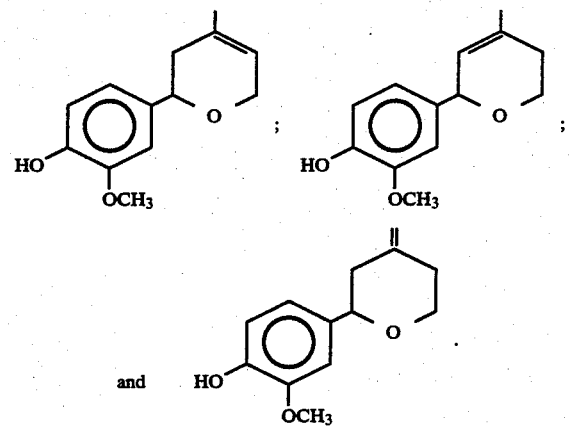

and

Referring to the drawings in FIGS. 12 and 13, the invention embodied therein comprises a device for forming scented polymer pellets (e.g., polyethylene, polypropylene or mixtures such as polyepsiloncaprolactone and polyethylene or polypropylene or copolymers of polyvinyl acetate and polyethylene or the like) which comprises a vat or container 210 into which a polymer or mixture of polymers admixed with one of the oxy-substituted-2-phenyl pyran derivatives of our invention is placed.

The container is closed by an air-tight lid 228 clamped to the container by clamps 265. A stirrer 273 traverses the lid or cover 228 in air-tight manner and is rotated in a suitable manner. The surrounding cylinder 212 having heating coils which are supplied with electrical current through cable 214 from a rheostat or control 216 is operated to maintain the temperature inside the container 210 such that the polymer such as polyethylene in the container will be maintained at a molten or liquid state. It has been found advantageous to employ a colorless, odorless polymer such as low density polyethylene with a viscosity ranging between about 180 and about 220 centistokes and having a melting point in the neighborhood of 220° F. The heater 212 is operated to maintain the upper portion of the container 210 within the temperature range of from 250°–350° F. An additional bottom heater 218 is regulated through a control 220 connected thereto through a connecting wire 222 to maintain the lower portion of the container 210 within the temperature range of from 250°–350° F.

In accordance with this aspect of the invention, a polymer such as polyethylene or polypropylene is added to the container 210 and is then heated from 10 to 12 hours whereafter an aroma imparting material containing at least one of the oxy-substituted-2-phenyl pyran derivatives of our invention or at least one of the oxy-substituted-2-phenyl pyran derivatives of our invention per se is quickly added to the melt. The mixture containing at least one of the oxy-substituted-2-phenyl pyran derivatives of our invention must be compatible with the polymer and forms a homogeneous liquid melt therewith. The heat resisting mixture generally containing from 10 to 40% by weight of the mixture of at least one of the oxy-substituted-2-phenyl pyran derivatives of our invention or a mixture thereof is added to container 210; the mixture is stirred for a few minutes, for example, 5–15 minutes, and maintained within the temperature range as indicated previously by the heating coils 212 and 218 respectively. The controls 216 and 220 are connected through cables 224 and 226 through a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and at least one of the oxy-substituted-2-phenyl pyran derivatives of our invention or mixture containing same will continuously drop or drip through the orifices 234 downwardly from the conduit 232. During this time, the temperature of the polymer and the perfumant mixture containing at least one of the oxy-substituted-2-phenyl pyran derivatives of our invention in the container 210 is accurately controlled so that a temperature in the range of from 210° up to 275° F. will be maintained in the material exiting in the conduit 232. The regulation of the temperature through the control 216 and the control 220 is essential in order to insure temperature balance to provide for the continuous dropping or dripping of the molten polymer and the perfumant containing at least one of the oxy-substituted-2-phenyl pyran derivatives of our invention through the orifices 234 at a rate which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

The present invention provides oxy-substituted-2-phenyl pyran derivatives defined according to the structure:

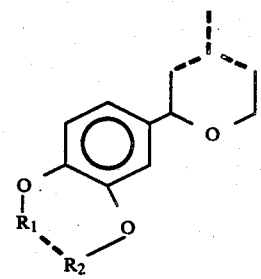

wherein:
(i) the dashed lines in the pyran ring each represent carbon-carbon single bonds; or one of the dashed lines is a carbon-carbon double bond and each of the other of the dashed lines is a carbon-carbon single bond;

(ii) $R_1$ is hydrogen and $R_2$ represents lower alkyl; or (iii) $R_1$ and $R_2$ taken together (as represented by the moiety:

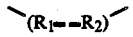

represents methylene.

The compounds and mixtures of compounds covered by the genus having the structure:

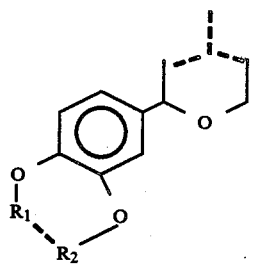

have utilities in perfumery; that is, in augmenting or enhancing the aroma of perfume compositions, colognes and perfumed articles including solid or liquid anionic, cationic, nonionic or zwitterionic detergents, fabric softener compositions, fabric softener articles, hair preparations, cosmetic powders and perfumed polymers.

The compounds defined according to the genus:

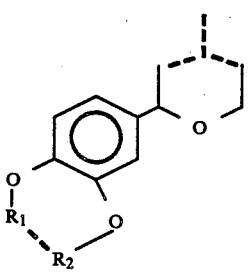

are prepared by reacting isoprenol having the structure:

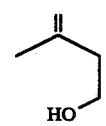

with an aldehyde defined according to the structure:

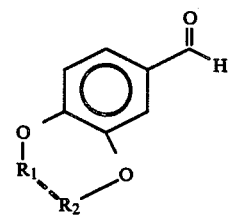

wherein:

(i) $R_1$ represents hydrogen and $R_2$ represents lower alkyl; or (ii) $R_1$ and $R_2$ represented by the moiety:

represents methylene according to the reaction:

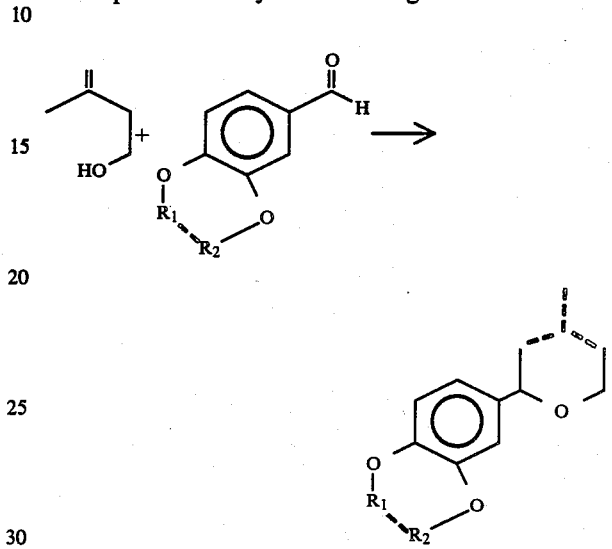

wherein in the pyran ring one of the dashed lines is a carbon-carbon double bond and each of the other of the dashed lines is a carbon-carbon single bond.

The resulting mixture of compounds defined according to the generic structure:

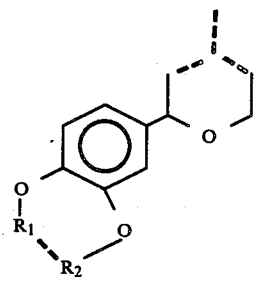

may be fractionally distilled and utilized "as is" for their perfumery properties or the resulting compounds may be further reacted whereby the double bond in the pyran ring is reduced to a carbon-carbon single bond as according to the reaction:

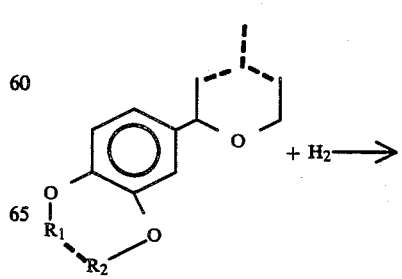

-continued

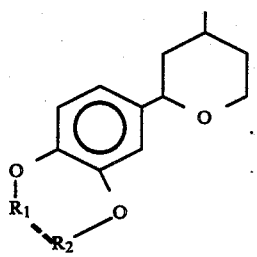

The reaction, to wit:

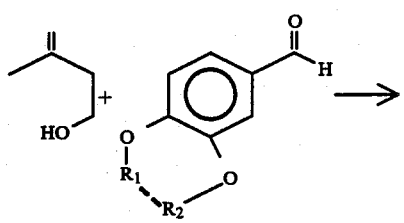

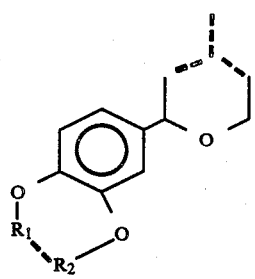

is carried out using a protonic acid catalyst such as para toluene sulphonic acid or methane sulphonic acid. The reaction is carried out at reflux conditions, removing the water of reaction. The reaction is carried out using a solvent which is inert to the reaction product but which will also aid in the removal of the water of reaction. Such a solvent is toluene, for example. The reaction is carried out, preferably, at atmospheric pressure at reflux conditions. Thus, the reaction temperature depends upon the particular solvent used. When using toluene, for example, the reaction is carried out at approximately 104°–115° C.

At the end of the reaction after all of the water of reaction is taken off, the reaction mass is neutralized such as with sodium acetate solution or sodium bicarbonate solution. The resulting product is then fractionally distilled to yield useful organoleptically acceptable product.

The mixture of compounds containing the unsaturated pyran ring defined according to the generic structure:

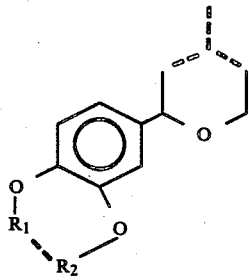

may, if desired, be hydrogenated according to the reaction:

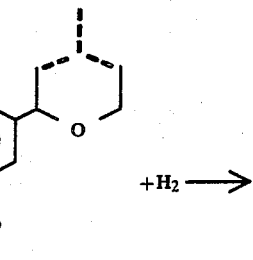

+H$_2$ →

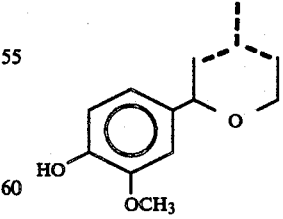

as set forth, supra. The hydrogenation reaction is preferably carried out at a temperature in the range of from about 40° C. up to about 50° C. and a pressure in the range of from about 300 psig up to about 500 psig. The hydrogenation reaction is carried out in the presence of a catalyst which will reduce the pyran ring double bond but which will not reduce the unsaturation in the phenyl moiety. Thus, for example, a 5% palladium on carbon catalyst is preferable in this reaction. Furthermore, the reaction is to be carried out in an inert solvent such as isopropyl alcohol. The reaction time may vary from about one hour up to about four hours. The reaction is preferably carried out in an appropriately pressured autoclave. At the end of the reaction, the reaction mass is fractionally distilled to yield organoleptically acceptable product.

The following table sets forth examples of compositions of matter produced according to the process of our invention and their respective perfumery utilities:

TABLE I

| Structure of Compounds Produced | Perfumery Utilities |
|---|---|
| The mixture of compounds defined according to the structure: wherein one of the dashed lines is a carbon-carbon double bond and each of the other of the dashed lines is a carbon-carbon single bond produced according to Example I, bulked fractions 12–15. | A spicy, rose, vanilla-like, and smokey aroma profile with carnation, rose, guiacwood, balsamic, natural sweet and vanilla topnotes. |

TABLE I-continued

| Structure of Compounds Produced | Perfumery Utilities |
|---|---|
| Compound defined according to the structure: 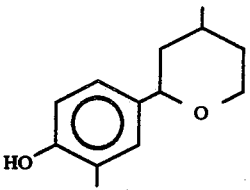 prepared according to Example II, bulked fractions 2-12. | A spicy, nutmeg and woody aroma profile with smokey, guiacwood and woody topnotes. |
| Mixture of compounds defined according to the structure: 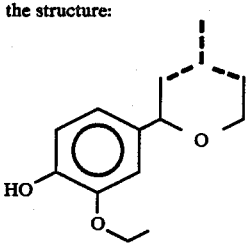 wherein, in the mixture in each of the compounds one of the dashed lines is a carbon-carbon double bond and each of the other of the dashed lines is a carbon-carbon single bond prepared according to Example III, bulked fractions 11-15. | A vanilla, tonka absolute-like, woody, spicy and balsamic aroma profile with sweet, vanilla, balsamic and musky topnotes. |
| Mixture of compounds defined according to the structure: 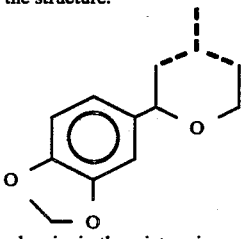 wherein, in the mixture in each of the compounds one of the dashed lines is a carbon-carbon double bond and each of the other of the dashed lines is a carbon-carbon single bond prepared according to Example IV, bulked fractions 3 and 4. | A floral, rose and spicy aroma profile with fruity, floral and rose topnotes. |

As stated, supra, the oxy-substituted-2-phenyl pyran derivatives of our invention can be used to contribute spicy, floral, rose, vanilla-like, smokey, nutmeg, woody, tonka absolute-like and balsamic aroma nuances with carnation, floral, rose, guiacwood, balsamic, natural sweet, vanilla, smokey, woody, musky and fruity topnotes to perfume compositions, perfumed articles and colognes with the perfumed articles being such materials as solid or liquid anionic, cationic, nonionic or zwitterionic detergents, perfumed polymers, fabric softener compositions, fabric softener articles, optical brighteners, fabric conditioners, hair preparations, shampoos and hair sprays. As olfactory agents the oxy-substituted-2-phenyl pyran derivatives of our invention can be formulated into or used as components of a "perfume composition".

The term "perfume composition" is used herein to mean a mixture of organic compounds including, for example, alcohols, aldehydes, ketones, nitriles, ethers, other than the oxy-substituted-2-phenyl pyran derivatives of our invention, lactones, ester, carbonates and, frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top notes which are usually low-boiling, fresh-smelling materials.

In perfume compositions, the individual component will contribute its particular olfactory characteristics, but the ovrall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of one or more of the oxy-substituted-2-phenyl pyran derivatives of our invention which will be effective in perfume compositions depends on many factors including the other ingredients, their amounts and the effects which are desired. It has been found that perfume compositions containing as little as 0.1% of at least one of the oxy-substituted-2-phenyl pyran derivatives of our invention or even less and perfume compositions containing as much as 70% of one or more of the oxy-substituted-2-phenyl pyran derivatives of our invention can be used to impart interesting and intense spicy, floral, rose, vanilla-like, smokey, nutmeg, woody, tonka absolute-like and balsamic aroma nuances with carnation, floral, rose, guiacwood, balsamic, natural sweet, vanilla, smokey, woody, musky and fruity topnotes to perfume compositions, colognes and perfumed articles. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70% as stated, supra, and will depend on considerations of cost, nature of the end product and the effect desired on the finished product and particular fragrance sought.

Thus, one or more the oxy-substituted-2-phenyl pyran derivatives of our invention can be used alone or in a perfume composition as an olfactory component, in solid or liquid anionic, cationic, nonionic or zwitterionic detergents (including hand soaps), perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler, or such as a solid or liquid anionic, cationic, nonionic or zwitterionic detergent or such as a cosmetic powder, as little as 0.01% of one or more of the oxy-substituted-2-phenyl pyran derivatives of our invention will suffice to provide an intense spicy, floral, rose, vanilla-like, smokey, nutmeg, woody, tonka absolute-like and balsamic aroma profile with with carnation, floral, rose, guiacwood, balsamic, natural sweet, vanilla, smokey, woody, musky and fruity topnotes. Generally, no more than 0.8% of one or more of the oxy-substituted-2-phenyl pyran derivatives of our invention is required. Thus, the range of the oxy-substituted-2-phenyl pyran derivatives of our invention in perfumed articles may vary from about 0.01% up to about 0.8%.

In addition, the perfume compositions of our invention can contain a vehicle or carrier for the oxy-substituted-2-phenyl pyran derivatives of our invention alone or with other ingredients. The vehicle can be a liquid such as an alcohol such as ethanol, a glycol such as propylene glycol or the like. The carrier can be an absorbent solid such as a gum (e.g., xanthan gum or gum arabic) or components for encapsulating the composition as by coacervation using gelatin or by forming a polymeric shell around a liquid perfume center by means of the use of a urea formaldehyde prepolymer.

The following Examples I, II, III and IV set forth processes for preparing the oxy-substituted-2-phenyl pyran derivatives of our invention. Example V and the following examples set forth methods for using the oxy-substituted-2-phenyl pyran derivatives of our invention for their organoleptic properties.

Unless otherwise indicated, all parts and percentages are by weight.

EXAMPLE I

Preparation of
2-Methoxy-4-(tetrahydro-4-methylene-2H-pyran-2-yl)phenol and
2-Methoxy-4-(dihydro-4-methyl-2H-pyran-2-yl)phenol Reaction:

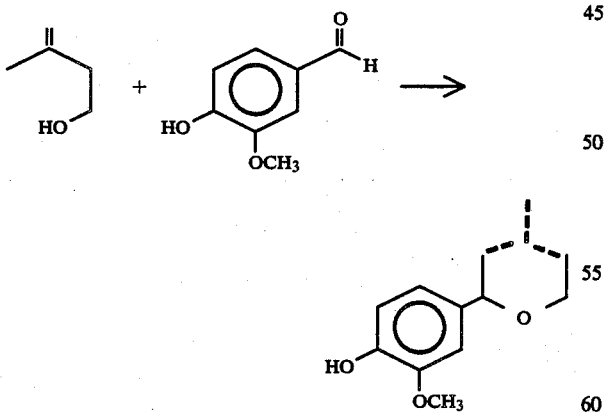

(wherein, in the pyran ring of one of the dashed lines is a carbon-carbon double bond and each of the other of the dashed lines is a carbon-carbon single bond).

Into a 1 liter reaction vessel equipped with stirrer, reflux condenser, thermometer and Bidwell water removal apparatus is placed 260 grams of toluene and 0.25 grams of para toluene sulphonic acid. The reaction mass is heated to reflux (104° C.) and over a 50 minute period a mixture of 167 grams of vanillin and 110 grams of isopropanol dissolved in 150 grams of toluene is added while removing water of reaction using the Bidwell apparatus. After 35 minutes a total of 21.6 grams of water is removed.

25 ml of 5% sodium acetate solution is added to the reaction mass. The reaction mass is then stripped of solvent and fractionally distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 151/ | 164/ | 1.0 | 9:1 |
| 2 | 155 | 160 | 1.0 | 9:1 |
| 3 | 162 | 183 | 1.0 | 9:1 |
| 4 | 153 | 204 | 1.0 | 4:1 |
| 5 | 65 | 221 | 1.0 | 4:1 |

The resulting product is then redistilled on a 24" vigreux column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 130/ | 160/ | 2.4 | 9:1 |
| 2 | 142 | 168 | 2.4 | 9:1 |
| 3 | 146 | 170 | 2.4 | 9:1 |
| 4 | 145 | 166 | 2.2 | 9:1 |
| 5 | 146 | 170 | 2.0 | 9:1 |
| 6 | 148 | 171 | 2.2 | 9:1 |
| 7 | 144 | 165 | 1.8 | 9:1 |
| 8 | 145 | 168 | 1.7 | 9:1 |
| 9 | 148 | 170 | 1.8 | 9:1 |
| 10 | 147 | 174 | 1.8 | 9:1 |
| 11 | 147 | 173 | 1.6 | 9:1 |
| 12 | 147 | 173 | 1.6 | 9:1 |
| 13 | 147 | 175 | 1.6 | 9:1 |
| 14 | 147 | 178 | 1.6 | 9:1 |
| 15 | 147 | 183 | 1.6 | 9:1 |
| 16 | 149 | 185 | 1.5 | 9:1 |
| 17 | 155 | 195 | 1.8 | 9:1 |
| 18 | 160 | 220 | 1.7 | 9:1 |

Fractions 12–15 are bulked and have a spicy, rose, vanilla-like and smokey aroma profile with carnation, rose, guiacwood, balsamic, natural sweet and vanilla topnotes.

FIG. 1 is the GLC profile for the crude reaction product prior to distillation. The peak indicated by reference numeral 10 is the peak for the vanillin reactant having the structure:

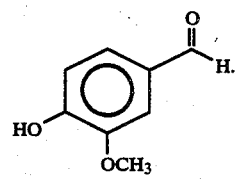

The peaks indicated by reference numerals 11, 12, 13 and 14 are the peaks for the compounds having the structures:

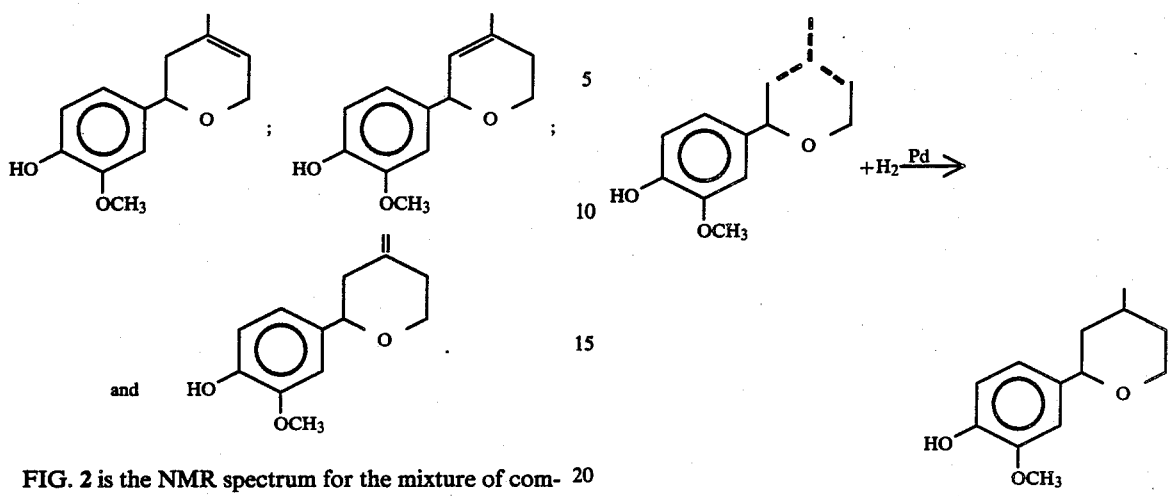

FIG. 2 is the NMR spectrum for the mixture of compounds having the structures:

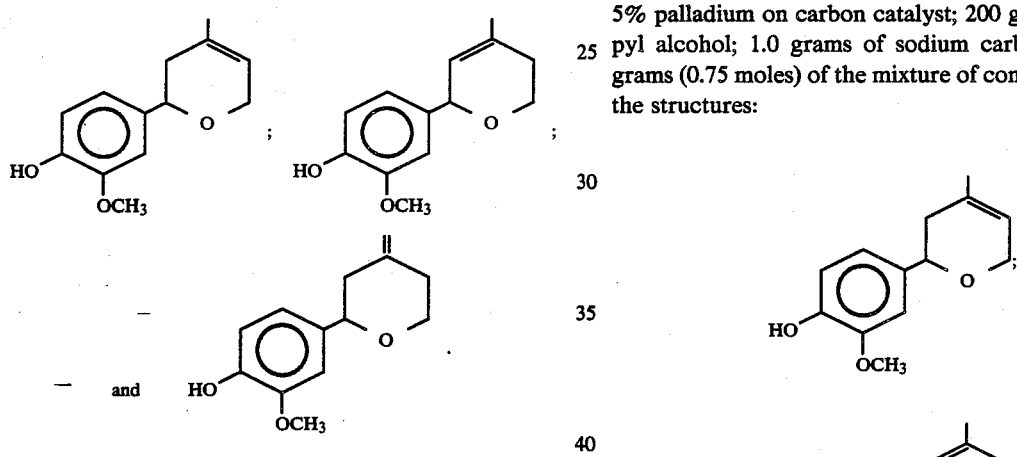

FIG. 3 is the infra-red spectrum for the mixture of compounds having the structures:

EXAMPLE II

Preparation of
2-Methoxy-4-(tetrahydro-4-methyl-2H-pyran-2-yl)phenol

Reaction:

Into a 1 liter zipper autoclave is placed 3.0 grams of a 5% palladium on carbon catalyst; 200 grams of isopropyl alcohol; 1.0 grams of sodium carbonate and 179 grams (0.75 moles) of the mixture of compounds having the structures:

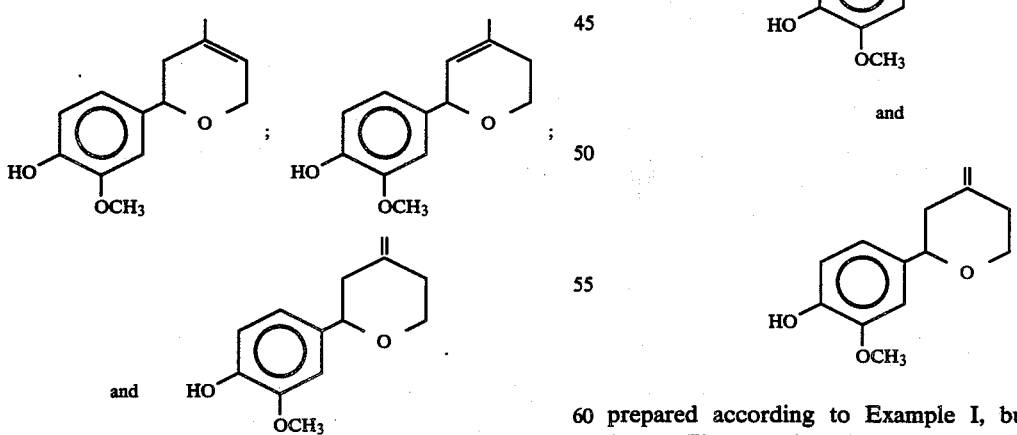

prepared according to Example I, bulked fractions 12–15. The autoclave is sealed and pressurized with hydrogen at a temperature of 40°–50° C. and a pressure of 350 psig for a period of three hours using up to 0.7 moles of hydrogen. At the end of the three hour period, the autoclave is cooled and opened and the reaction mass is filtered. The reaction mass is then distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 6/133 | 100/148 | 1.2 | 4:1 |
| 2 | 136 | 149 | 1.1 | 4:1 |
| 3 | 134 | 149 | 1.1 | 4:1 |
| 4 | 134 | 148 | 1.1 | 4:1 |
| 5 | 134 | 147 | 1.0 | 4:1 |
| 6 | 134 | 150 | 1.0 | 4:1 |
| 7 | 134 | 150 | 1.0 | 4:1 |
| 8 | 135 | 151 | 1.0 | 4:1 |
| 9 | 135 | 153 | 1.0 | 4:1 |
| 10 | 137 | 158 | 1.0 | 4:1 |
| 11 | 139 | 165 | 1.0 | 4:1 |
| 12 | 150 | 190 | 1.4 | 4:1 |
| 13 | 157 | 220 | 1.6 | 4:1 |

Fractions 2–12 are bulked and have a spicy, nutmeg and woody aroma profile with smokey, guiacwood and woody topnotes.

FIG. 4 is the GLC profile of the crude reaction product containing the compound having the structure:

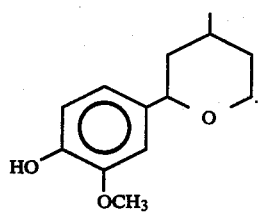

FIG. 5 is the NMR spectrum for the compound having the structure:

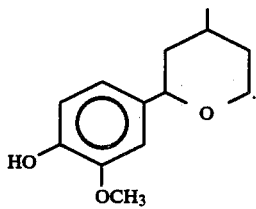

FIG. 6 is the IR spectrum for the compound having the structure:

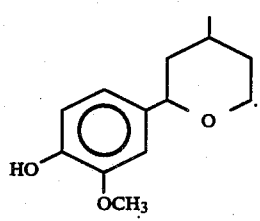

EXAMPLE III

Preparation of Mixture of
2-Ethoxy-4-(tetrahydro-4-methylene-2H-pyran)phenol
and
2-Ethoxy-4-(dihydro-4-methyl-2H-pyran-2-yl)phenol Reaction:

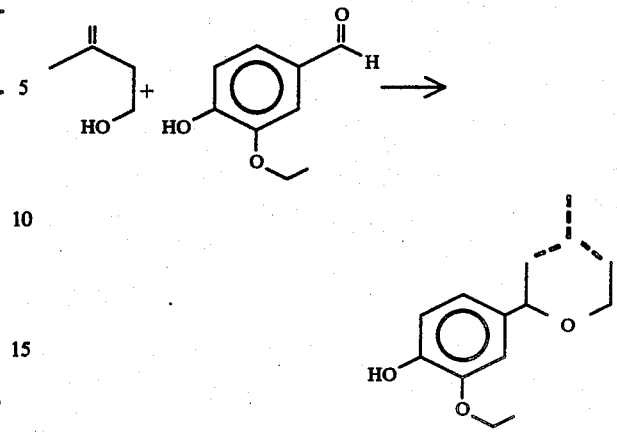

(wherein, in the pyran ring one of the dashed lines is a carbon-carbon double bond and each of the other of the dashed lines is a carbon-carbon single bond).

Into a 5 liter reaction flask equipped with Bidwell water trap, stirrer, condenser, thermometer and heating mantle is placed 1200 grams of toluene and 0.75 grams of methane sulphonic acid. The reaction mass is heated to reflux and over a period of 90 minutes a mixture of 499 grams (3 moles) of ethyl vanillin and 330 grams (3.8 moles) of isoprenol in 330 grams of toluene is added to the reaction mass with stirring. The resulting product at reflux is stirred for a period of 30 minutes while refluxing. The reaction mass is then cooled at 70° C., 200 grams of a 10% aqueous sodium carbonate solution is added thereto. 57 Grams of water is taken off during the reaction. The reaction mass is then washed with two volumes of a 5% aqueous sodium chloride solution.

The aqueous phase is separated from the organic phase. The organic phase is then fractionally distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 28/ | 103/ | 1.0 | 2:1 |
| 2 | 156 | 176 | 2.0 | 2:1 |
| 3 | 161 | 195 | 2.0 | 2:1 |
| 4 | 161 | 220 | 2.0 | 2:1 |
| 5 | 161 | 235 | 2.0 | 2:1 |

The resulting product is then redistilled on a 24" vigreux column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 155 | 165 | 2.4 | 9:1 |
| 2 | 155 | 165 | 2.4 | 9:1 |
| 3 | 145 | 164 | 1.4 | 9:1 |
| 4 | 145 | 165 | 1.2 | 9:1 |
| 5 | 147 | 171 | 1.0 | 9:1 |
| 6 | 148 | 172 | 0.80 | 9:1 |
| 7 | 148 | 172 | 0.80 | 9:1 |
| 8 | 147 | 173 | 0.80 | 4:1 |
| 9 | 146 | 173 | 0.78 | 4:1 |
| 10 | 146 | 177 | 0.78 | 3:1 |
| 11 | 148 | 182 | 0.78 | 3:1 |
| 12 | 148 | 182 | 0.78 | 3:1 |
| 13 | 149 | 197 | 0.78 | 3:1 |
| 14 | 153 | 213 | 0.78 | 3:1 |

Fractions 9–13 are bulked and bulked fractions 9–13 have a vanilla, tonka absolute-like, woody, spicy and balsamic aroma profile with sweet, vanilla, balsamic and musky topnotes.

FIG. 7 is the NMR spectrum for the mixture of compounds having the structures:

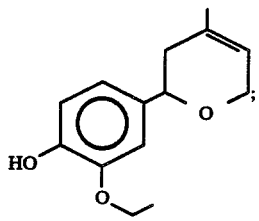

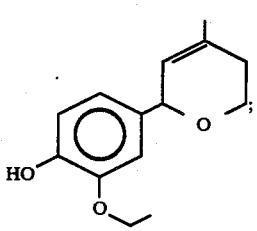

and

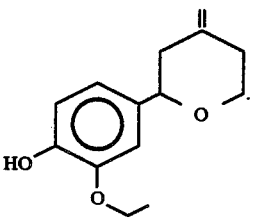

FIG. 8 is in the infra-red spectrum for the mixture of compounds having the structures:

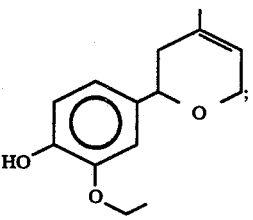

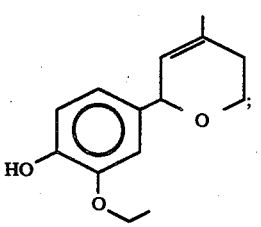

and

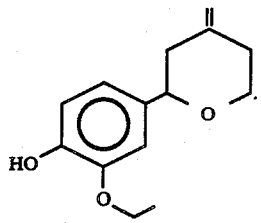

EXAMPLE IV

Preparation of
1,2-Methylenedioxy-4-(tetrahydro-4-methylene-2H-pyran-2yl)phenol and
1,2-methylenedioxy-4-(dihydro-4-methyl-2H-pyran-2-yl)phenol Reaction:

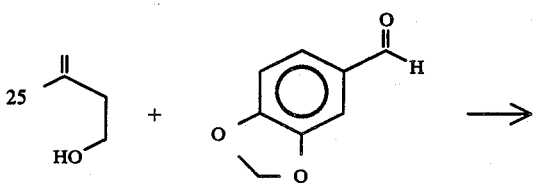

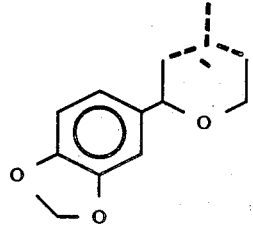

(wherein, in the pyran ring one of the dashed lines is a carbon-carbon double bond and each of the other of the dashed lines are carbon-carbon single bonds).

Into a 5 liter reaction flask equipped with stirrer, thermometer, reflux condenser, Bidwell water collection apparatus and addition funnel is placed 0.75 grams of methane sulphonic acid and 750 grams of toluene. The reaction mass is heated to reflux and over a period of two hours, 450 grams of isoprenol, 1750 grams of toluene and 600 grams of heliotropin having the structure:

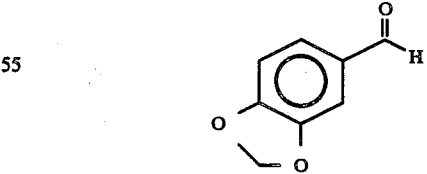

is added to the reaction mass while refluxing.

The reaction mass is continued to be stirred at reflux while removing water using the Bidwell apparatus for a period of six hours. 80 Grams of water is recovered. The reaction mass is then stirred for another 30 minutes and cooled. To the cooled reaction mass 200 grams of a 10% sodium carbonate solution is added. The reaction mass is then washed as follows:

(i) 2 volumes of 5% sodium carbonate (250 ml); and (ii) 2 volumes of 5% aqueous sodium chloride (250 ml).

The aqueous phase is separated from the organic phase and the organic phase is fractionally distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 96/ | 150/ | 4.0 | 4:1 |
| 2 | 128 | 150 | 3.0 | 4:1 |
| 3 | 129 | 145 | 1.8 | 1:2 |
| 4 | 130 | 148 | 1.8 | 1:2 |
| 5 | 130 | 153 | 1.6 | 1:2 |
| 6 | 132 | 168 | 1.8 | 1:2 |
| 7 | 140 | 2055 | 6.0 | 1:2 |
| 8 | 163 | 220 | 6.0 | 1:2 |

Fractions 3 and 4 are bulked and bulked fractions 3 and 4 have a floral, rose and spicy aroma profile with fruity, floral and rose topnotes.

FIG. 9 is the GLC profile for the crude reaction product prior to distillation (Conditions: 10% SE-30 column programmed at 80°-220° C. at 8° C. per minute). The crude reaction product contains the compounds having the structures:

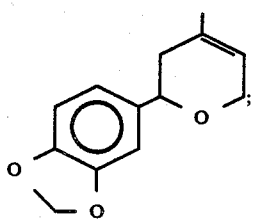

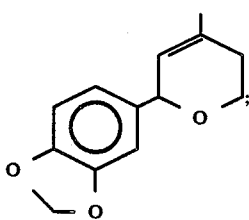

and

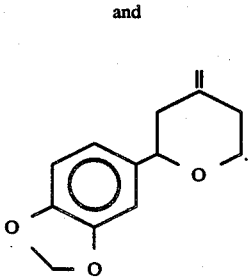

FIG. 10 is the NMR spectrum for the compounds having the structures:

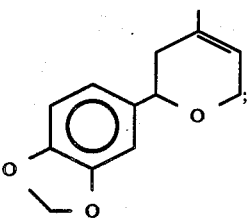

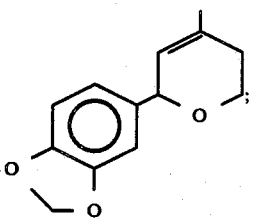

and

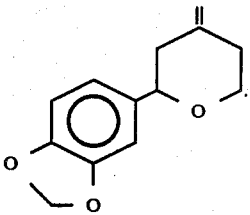

FIG. 11 is the infra-red spectrum for the compounds having the structures:

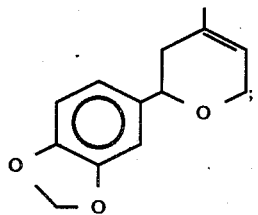

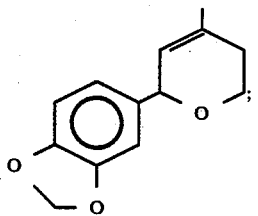

and

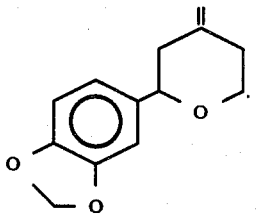

EXAMPLE V

Herbal Fragrance Formulations Using Products Prepared According to Examples I, II, III and IV

| Ingredients | Parts by Weight | | | |
|---|---|---|---|---|
| | V(A) | V(B) | V(C) | V(D) |
| Amyl cinnamic aldehyde | 20 | 20 | 20 | 20 |
| Phenyl acetaldehyde dimethyl acetal | 4 | 4 | 4 | 4 |
| Thyme oil white | 8 | 8 | 8 | 8 |
| Sauge sclaree French | 8 | 8 | 8 | 8 |
| Galbanum oil | 4 | 4 | 4 | 4 |
| Juniper berry oil | 10 | 10 | 10 | 10 |
| Methyl octin carbonate | 4 | 4 | 4 | 4 |
| Linalyl acetate | 2 | 2 | 2 | 2 |
| Dihydro methyl jasmonate | 10 | 10 | 10 | 10 |
| The bicyclononenyl carbonate mixture prepared according to Example II, bulked distillation fractions 10-14 of U.S. Letters Pat. No. 4,673,533. | 10 | 10 | 10 | 10 |
| Mixture of compounds defined according to the structure: [structure with HO, OCH₃] prepared according to Example I, bulked fractions 12-15. | 8 | 0 | 0 | 0 |
| Compound having the structure: [structure with HO, OCH₃] prepared according to Example II, bulked distillation fractions 2-12. | 0 | 8 | 0 | 0 |
| Mixture of compounds defined according to the structure: [structure with HO, OCH₂CH₃] bulked distillation fractions 9-13. | 0 | 0 | 8 | 0 |
| Mixture of compounds defined according to the structure: [structure] prepared according to Example IV, bulked distillation fractions 3 and 4. | 0 | 0 | 0 | 8 |

The composition of matter containing the product of Example I adds to this herbal fragrance formulation spicy, rose, vanilla-like and smokey undertones and carnation, rose, guiacwood, balsamic, natural sweet and vanilla topnotes. Accordingly, the perfume composition of Example V(A) can be described as "herbal with spicy, rose, vanilla-like and smokey undertones and carnation, rose, guiacwood, balsamic, natural sweet and vanilla" topnotes.

The composition of matter of Example II adds to the herbal fragrance spicy, nutmeg and woody undertones with smokey, guiacwood and woody topnotes. Accordingly, the perfume composition of Example V(B) can be described as "herbal with spicy, nutmeg and woody undertones and smokey, guiacwood and woody" topnotes.

The composition of matter of Example III adds to the herbal fragrance vanilla, tonka absolute-like, woody, spicy and balsamic undertones and sweet, vanilla, balsamic and musky topnotes. Accordingly, the perfume composition of Example V(C) can be described as "herbal with vanilla, tonka absolute-like, woody, spicy and balsamic undertones and sweet, vanilla, balsamic and musky" topnotes.

The composition of matter of Example IV adds to the herbal fragrance a floral, rose and spicy undertone profile with fruity, floral and rose topnotes. Accordingly, the perfume composition of Example V(D) can be described as "herbal with floral, rose and spicy undertones and fruity, floral and rose" topnotes.

EXAMPLE VI

Preparation of Cosmetic Powder Compositions

Cosemetic powder compositions are prepared by mixing in a ball mill 100 grams of talcum powder with 0.25 grams of each of the substances set forth in Table II below. Each of the cosmetic powder compositions has an excellent aroma as described in Table II below:

| Substance | Aroma Description |
|---|---|
| Mixture of compounds defined according to the structure: | A spicy, rose, vanilla-like and smokey aroma profile with carnation, rose, guiacwood, balsamic, natural sweet and vanilla topnotes. |

| Substance | Aroma Description |
|---|---|
| 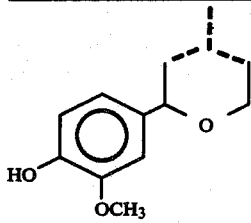 prepared according to Example I, bulked distillation fractions 12-15. | A spicy, nutmeg and woody aroma profile, with smokey, guiacwood and woody topnotes. |
| 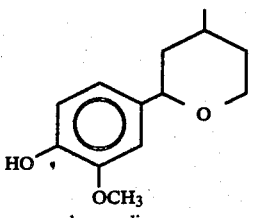 prepared according to Example II, bulked distillation fraction 2-12. | |
| Mixture of compounds defined according to the structure: 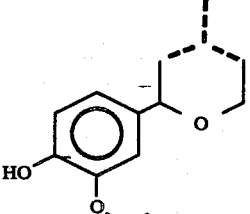 prepared according to Example III, bulked distillation fractions 9-13. | A vanilla, tonka absolut-like, woody, spicy and balsamic aroma profile with sweet, vanilla, balsamic and musky topnotes. |
| Mixture of compounds defined according to the structure: 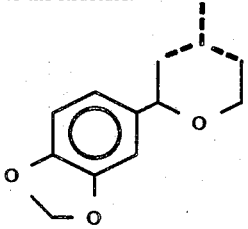 prepared according to Example IV, bulked distillation fractions 3 and 4. | A floral, rose and spicy aroma profile with fruity, floral and rose topnotes. |
| Perfume composition of Example V(A). | Herbal, with spicy, rose, vanilla-like, and smokey undertones and carnation, rose, guiacweed, balsamic, natural sweet and vanilla topnotes. |
| Perfume composition of Example V(B). | Herbal, with spicy, nutmeg and woody undertones and smokey, guiacwood and woody topnotes. |
| Perfume composition of Example V(C). | Herbal, with vanilla, tonka absolute-like, woody, spicy and balsamic undertones and sweet, vanilla, balsamic and musky topnotes |
| Perfume composition of Example V(D). | Herbal, with floral, rose and spicy undertones and fruity, floral and rose topotes. |

EXAMPLE VII

Perfumed Liquid Detergents

Concentrated liquid detergents (lysine salt of n-dodecylbenzene sulfonic acid as more specifically described in U.S. Pat. No. 3,948,818 issued April 6, 1976 incorporated by reference herein) with aroma nuances as set forth in Table II of Example VI, are prepared containing 0.10%, 0.15%, 0.20%, 0.25%, 0.30% and 0.35% of the substance set forth in Table II of Example VI. They are prepared by adding and homogeneously mixing the appropriate qunatity of substance set forth in Table II of Example VI in the liquid detergent. The detergents all possess excellent aromas as set forth in Table II of Example VI, the intensity increasing with greater concentrations of substance as set forth in Table II of Example VI.

EXAMPLE VIII

Preparation of Colognes and Handkerchief Perfumes

Compositions as set forth in Table II of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfurms at concentrations of 15%, 20%, 25%, and 30% (in 80%, 85%, 90% and 95% aqueous food grade ethanol solutions). Distinctive and definite fragrances as set forth in Table II of Example VI are imparted to the colognes and to the handkerchief perfumes at all levels indicated.

EXAMPLE IX

Preparation of Soap Compositions

One hundred grams of soap chips (per sample)-(IVORY ®—produced by the Proctor and Gamble Company, Cincinnati, Ohio), are each mixed with one gram samples of substances as set forth in Table II of Example VI until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling, manifest aromas as set forth in Table II of Example VI.

EXAMPLE X

Preparation of Solid Detergent Compositions

Detergents are prepared using the following ingredients according to Example I of Canadian Pat. No. 1,007,948 (incorporated by reference herein):

| Ingredient | Parts by Weight |
|---|---|
| NEODOL ® 45-11 (a $C_{14}$–$C_{15}$ alcohol ethoxylated with 11 moles of ethylene oxide | 12 |
| Sodium carbonate | 55 |
| Sodium citrate | 20 |

| Ingredient | Parts by Weight |
|---|---|
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogan 448 (m.p. about 140° F.) as the substrate coating; and
3. An outer coating having the following formulation (m.p. about 150° F.):
57%—$C_{20-22}$ HAPS
22%—isopropyl alcohol
20%—antistatic agent
1%—of one of the substances as set forth in Table II of Example VI.

Fabric softening compositions prepared according to Example I at column 15 of U.S. Pat. No. 3,632,396 having aroma characteristics as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example VI, supra.

EXAMPLE XII

Hair Spray Formulations

The following hair spray formulation is prepared by first dissolving PVP/VA E-735 copolymer manufactured by the GAF Corporation of 140 West 51st Street, New York, New York in 91.62 grams of 95% food grade ethanol. 8.0 Grams of the polymer is dissolved in the alcohol. The following ingredients are added to the PVP/VA alcoholic solution:

| | Weight Percent |
|---|---|
| Dioctyl sebacate | 0.05 |
| Benayl alcohol | 0.10 |
| Dow Corning 473 fluid prepared by the Dow Corning Corporation | 0.10 |
| TWEEN ® surfactant | 0.03 |
| (prepared by ICI America Corporation) | |
| One of the perfumery substances as set forth in Table II of Example VI | 0.10 |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

Conditioning Shampoos

A Monamid CMA (prepared by the Mona Industries Company) 3.0 weight percent) is melted with 2.0 weight percent coconut fatty acid (prepared by Proctor and Gamble Company of Cincinnati, Ohio); 1.0 weight percent ethylene gylcol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT®755N polymer (manufactured by GAF Corporation of 140 West 51st Street, New York, New York)(5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

EXAMPLE XIV

Scented polyethylene pellets having a pronounced scent as set forth in Table II of Example VI are prepared as follows:

75 Pounds of polyethylene of a melting point of about 200° F. are heated to about 230° F. in a container of the kind illustrated in FIGS. 12 and 13. 25 Pounds of each of the perfumery materials of Table II of Example VI, supra, are then added quickly to the liquified polyethylene. The lid 228 is put in place and the agitating means 273 are actuated. The temperature is maintained at about 225° F. and the mixing is then continued for about 5-15 minutes. The value "V" is then opened to allow flow of the molten polyethylene enriched with each of the aroma containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table II of Example VI, supra, are then formed. Analysis demonstrates that the pellets contain about 25% of each of the perfume substances of Table II of Example VI so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table II of Example VI, supra. The sheet are also fabricated into garbage bags which have aromas as set forth in Table II of Example VI, supra.

What is claimed is:

1. An oxy-substituted-2-phenyl pyran derivative defined according to the structure:

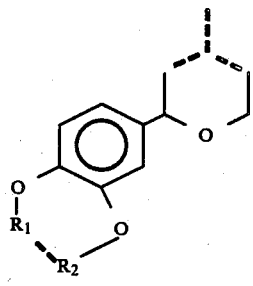

wherein:
(i) the dashed lines each represent carbon-carbon single bonds; or one of the dashed lines is a carbon-carbon double bond and the other of the dashed lines is a carbon-carbon single bond;
(ii) wherein $R_1$ is hydrogen and $R_2$ is lower alkyl; or
(iii) $R_1$ and $R_2$ taken together as represented by the moiety:

represent methylene.

2. A mixture of compounds defined according to the structure:

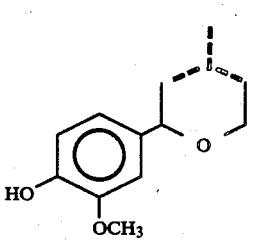

wherein, in the mixture in each of the compounds one of the dashed lines is a carbon-carbon double bond and each of the other of the dashed lines are carbon-carbon single bonds.

3. A mixture of compounds defined according to the structure:

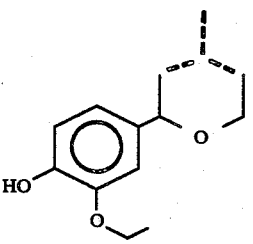

wherein, in the mixture, in each of the compounds one of the dashed lines is a carbon-carbon double bond and each of the other of the dashed lines are carbon-carbon single bonds.

4. A mixture of compounds defined according to the structure:

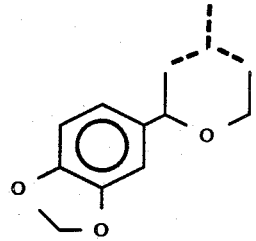

wherein, in the mixture in each of the compounds one of the dashed lines is a carbon-carbon double bond and each of the other of the dashed lines is a carbon-carbon single bond.

5. The compound having the structure:

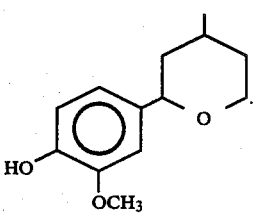

6. The process for augmenting or enhancing the aroma of a perfume composition, cologne or perfumed article comprising the step of intimately admixing with a perfume base, cologne base or a perfumed article base, an aroma augmenting or enhancing quantity of at least one oxy-substituted-2-phenyl pyran derivative defined according to claim 1.

7. The process of claim 6 wherein the oxy-substituted-2-phenyl pyran derivative is added to a perfume composition.

8. The process of claim 6 wherein the oxy-substituted-2-phenyl pyran derivative is added to a cologne.

9. The process of claim 6 wherein the oxy-substituted-2-phenyl pyran derivative is added to a perfumed article and the perfumed article is a perfumed polymer.

10. The process of claim 6 wherein the oxy-substituted-2-phenyl pyran derivative is added to a perfumed article and the perfumed article is a solid or liquid anionic, cationic, nonionic or zwitterionic detergent.

11. The process of claim 6 wherein the oxy-substituted-2-phenyl pyran derivative is added to a perfumed article and the perfumed article is a fabric softener composition or fabric softener article.

12. The process of claim 6 wherein the oxy-substituted-2-phenyl pyran derivative is added to a perfumed article and the perfumed article is a cosmetic powder.

13. A perfume composition comprising a perfume base and intimately admixed therewith, an aroma augmenting or enhancing quantity of at least one oxy-substituted-2-phenyl pyran derivative defined according to claim 1.

14. A cologne composition comprising water, ethanol and an aroma augmenting or enhancing quantity of at least one oxy-substituted-2-phenyl pyran derivative defined according to claim 1.

15. A perfumed polymer comprising a polymer base and intimately admixed therewith, an aroma augmenting or enhancing quantity of at least one oxy-substituted-2-phenyl pyran derivative defined according to claim 1.

* * * * *